(12) United States Patent
Locke

(10) Patent No.: US 11,266,770 B2
(45) Date of Patent: Mar. 8, 2022

(54) WOUND THERAPY SYSTEM WITH FLUID CANISTER VOLUME DETECTION

(71) Applicant: KCI Licensing, Inc., San Antonio, TX (US)

(72) Inventor: Christopher Brian Locke, Bournemouth (GB)

(73) Assignee: KCI Licensing, Inc., San Antonio, TX (US)

( * ) Notice: Subject to any disclaimer, the term of this patent is extended or adjusted under 35 U.S.C. 154(b) by 342 days.

(21) Appl. No.: 16/365,481

(22) Filed: Mar. 26, 2019

(65) Prior Publication Data
US 2020/0289719 A1    Sep. 17, 2020

Related U.S. Application Data

(60) Provisional application No. 62/816,704, filed on Mar. 11, 2019.

(51) Int. Cl.
*A61M 1/00*    (2006.01)

(52) U.S. Cl.
CPC ............ *A61M 1/0003* (2013.01); *A61M 1/90* (2021.05); *A61M 2205/3334* (2013.01);
(Continued)

(58) Field of Classification Search
CPC ........ A61M 1/0003; A61M 1/07; A61M 1/90; A61M 2205/3337; A61M 2205/3379;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Kai H Weng
*Assistant Examiner* — Seth Han

(57) ABSTRACT

A wound therapy system includes a wound dressing fluidly connected to a fluid canister. The fluid canister is attached to a canister receiving attachment of a housing structure. A pump is fluidly coupled to the canister and is configured to draw a negative pressure within an interior of the canister. A controller of the wound therapy system is configured to operate the pump to apply a vacuum to the interior of the canister and to obtain one or more measurements representative of at least one or a flow rate of air that is exhausted from the canister interior, a pressure within the canister interior and pump ripple. The controller is configured to estimate the volume of the canister based on the comparison of the measured parameters against model data stored by the controller that is representative of the operation of the therapy system with canisters of varying volumes.

24 Claims, 14 Drawing Sheets

(52) U.S. Cl.
CPC ............... *A61M 2205/3379* (2013.01); *A61M 2205/502* (2013.01); *A61M 2205/52* (2013.01); *A61M 2205/583* (2013.01)

(58) Field of Classification Search
CPC ............ A61M 2205/52; A61M 1/0088; A61M 2205/3331; A61M 2205/3334; A61M 2205/50
USPC ...................................................... 604/319
See application file for complete search history.

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 9,408,954 B2 * | 8/2016 | Gordon ................. A61M 1/784 |
| 9,844,485 B2 * | 12/2017 | Locke .................. A61N 1/0468 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2013/0150813 A1 | 6/2013 | Gordon |
| 2016/0015872 A1 | 1/2016 | Luckemeyer |
| 2018/0135235 A1 * | 5/2018 | Yu ........................... D06F 58/34 |
| 2020/0061253 A1 * | 2/2020 | Long ...................... A61M 1/73 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3222300 A1 | 9/2017 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philadelphia, PA, USA.

John Masters; "Reliable, Inexpensive and Simple Suction Dressings"; Letter to the Editor, British Journal of Plastic Surgery, 1998,

(56) References Cited

OTHER PUBLICATIONS vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
International Search Report and Written Opinion in International Application No. PCT/US2019/024133, dated Dec. 2, 2019.

* cited by examiner

| 1000 mL ||
|---|---|
| Time (s) | Pressure (mmHg) |
| 0 | -0.2 |
| 2 | -0.2 |
| 4 | -0.2 |
| 6 | -0.2 |
| 8 | -0.3 |
| 10 | -0.2 |
| 12 | -0.3 |
| 14 | 17.6 |
| 16 | 28.3 |
| 18 | 47.9 |
| 20 | 68.3 |
| 22 | 113.9 |
| 24 | 112.9 |
| 26 | 112.3 |
| 28 | 116.7 |
| 30 | 125.4 |
| 32 | 120.1 |
| 34 | 122.3 |
| 36 | 121.3 |
| 38 | 121.9 |
| 40 | 121.6 |
| 42 | 129.8 |
| 44 | 125.6 |
| 46 | 125.4 |
| 48 | 126 |
| 50 | 125.9 |
| 52 | 125.8 |
| 54 | 125.6 |
| 56 | 125.4 |
| 58 | 125.3 |
| 60 | 125.3 |
| 62 | 125.2 |
| 64 | 125.1 |
| 66 | 125.1 |
| 68 | 124.9 |
| 70 | 124.7 |
| 72 | 123.9 |
| 74 | 109 |
| 76 | 101.3 |

| 500 mL ||
|---|---|
| Time (s) | Pressure (mmHg) |
| 0 | 0.8 |
| 2 | 0.7 |
| 4 | 0.5 |
| 6 | 0.3 |
| 8 | 0.2 |
| 10 | 0.2 |
| 12 | 22 |
| 14 | 64.3 |
| 16 | 91.4 |
| 18 | 90.6 |
| 20 | 107 |
| 22 | 118.9 |
| 24 | 116.5 |
| 26 | 118.4 |
| 28 | 119.4 |
| 30 | 121 |
| 32 | 120.3 |
| 34 | 121.4 |
| 36 | 121.3 |
| 38 | 121.1 |
| 40 | 122.4 |
| 42 | 124.1 |
| 44 | 123.8 |
| 46 | 125.1 |
| 48 | 125.1 |
| 50 | 125.2 |
| 52 | 125.3 |
| 54 | 125 |
| 56 | 125 |
| 58 | 125 |
| 60 | 124.9 |
| 62 | 124.8 |
| 64 | 124.8 |
| 66 | 124.8 |
| 68 | 124.6 |
| 70 | 124.5 |
| 72 | 102.8 |
| 74 | 92.3 |

| 300 mL ||
|---|---|
| Time (s) | Pressure (mmHg) |
| 0 | 0.1 |
| 2 | 0.2 |
| 4 | 0.4 |
| 6 | 0.7 |
| 8 | 0.3 |
| 10 | 0.2 |
| 12 | 0.8 |
| 14 | 28.1 |
| 16 | 50 |
| 18 | 73.1 |
| 20 | 110.7 |
| 22 | 128.3 |
| 24 | 115.4 |
| 26 | 117 |
| 28 | 118.8 |
| 30 | 119.8 |
| 32 | 121 |
| 34 | 120.8 |
| 36 | 121.6 |
| 38 | 121.6 |
| 40 | 121.6 |
| 42 | 123.3 |
| 44 | 123.2 |
| 46 | 124.3 |
| 48 | 127.3 |
| 50 | 125.4 |
| 52 | 125.2 |
| 54 | 125.2 |
| 56 | 125.4 |
| 58 | 125.3 |
| 60 | 125.3 |
| 62 | 125.5 |
| 64 | 125.3 |
| 66 | 125.3 |
| 68 | 125.2 |
| 70 | 112.9 |
| 72 | 88.5 |
| 74 | 80.7 |
| 76 | 55.9 |

FIG. 3B

| 1000 mL | | | | 500 mL | | | | 300 mL | | | |
|---|---|---|---|---|---|---|---|---|---|---|---|
| Time (s) | Flow (L/min) | Time (s) | Flow (L/min) | Time (s) | Flow (L/min) | Time (s) | Flow (L/min) | Time (s) | Flow (L/min) | Time (s) | Flow (L/min) |
| 0.25 | 0 | \-continued | | 0.29 | -0.01 | \-continued | | 0.31 | 0 | \-continued | |
| 0.57 | 0 | 14.6 | 0.49 | 0.6 | -0.01 | 14.64 | 0.32 | 0.62 | 0 | 14.66 | 0.74 |
| 0.88 | 0 | 14.92 | 1.2 | 0.91 | -0.01 | 14.95 | 0.62 | 0.93 | 0 | 14.97 | 0.34 |
| 1.19 | 0 | 15.23 | 0.76 | 1.22 | -0.01 | 15.26 | 0.52 | 1.24 | 0 | 15.28 | 0.69 |
| 1.5 | 0 | 15.54 | 1.02 | 1.53 | -0.01 | 15.57 | 0.52 | 1.56 | 0 | 15.59 | 0.35 |
| 1.81 | 0 | 15.85 | 0.96 | 1.85 | -0.01 | 15.89 | 0.41 | 1.87 | 0 | 15.91 | 0.66 |
| 2.13 | 0 | 16.16 | 0.79 | 2.16 | -0.01 | 16.2 | 0.7 | 2.18 | 0 | 16.22 | 0.38 |
| 2.44 | 0 | 16.48 | 1.19 | 2.47 | -0.01 | 16.51 | 0.29 | 2.49 | 0 | 16.53 | 0.38 |
| 2.75 | 0 | 16.79 | 0.66 | 2.78 | -0.01 | 16.82 | 0.74 | 2.8 | 0 | 16.84 | 0.74 |
| 3.06 | 0 | 17.1 | 1.21 | 3.09 | -0.01 | 17.13 | 0.21 | 3.11 | 0 | 17.15 | 0.35 |
| 3.37 | 0 | 17.41 | 1.21 | 3.41 | -0.01 | 17.45 | 0.64 | 3.43 | 0 | 17.47 | 0.72 |
| 3.69 | 0 | 17.72 | 0.63 | 3.72 | -0.01 | 17.76 | 0.19 | 3.74 | 0 | 17.78 | 0.38 |
| 4 | 0 | 18.04 | 1.24 | 4.03 | -0.01 | 18.07 | 0.41 | 4.05 | 0 | 18.09 | 0.64 |
| 4.31 | 0 | 18.35 | 0.45 | 4.34 | -0.01 | 18.38 | 0.41 | 4.36 | 0 | 18.4 | 0.4 |
| 4.62 | 0 | 18.66 | 1.15 | 4.65 | -0.01 | 18.69 | 0.12 | 4.67 | 0 | 18.71 | 0.67 |
| 4.93 | 0 | 18.97 | 0.44 | 4.97 | -0.01 | 19.01 | 0.22 | 4.99 | 0 | 19.03 | 0.21 |
| 5.25 | 0 | 19.28 | 0.92 | 5.28 | 0 | 19.32 | 0.07 | 5.3 | 0 | 19.34 | 0.5 |
| 5.56 | 0 | 19.6 | 0.35 | 5.59 | 0 | 19.63 | 0.02 | 5.61 | 0 | 19.65 | 0.5 |
| 5.87 | 0 | 19.91 | 0.68 | 5.9 | 0 | 19.94 | 0.1 | 5.92 | 0 | 19.96 | 0.16 |
| 6.18 | 0 | 20.22 | 0.68 | 6.21 | 0.01 | 20.25 | 0.02 | 6.23 | 0 | 20.27 | 0.4 |
| 6.49 | 0 | 20.53 | 0.25 | 6.53 | 0.01 | 20.56 | 0.12 | 6.55 | 0 | 20.59 | 0.13 |
| 6.81 | 0 | 20.84 | 0.65 | 6.84 | 0.47 | 20.88 | 0.03 | 6.86 | 0 | 20.9 | 0 |
| 7.12 | 0 | 21.16 | 0.21 | 7.15 | 0.12 | 21.19 | 0 | 7.17 | 0 | 21.21 | 0.11 |
| 7.43 | 0 | 21.47 | 0.51 | 7.46 | 0.7 | 21.5 | 0.12 | 7.48 | 0 | 21.52 | 0.02 |
| 7.74 | 0 | 21.78 | 0.13 | 7.77 | 0.2 | 21.81 | 0.12 | 7.79 | 0 | 21.83 | 0.14 |
| 8.05 | 0 | 22.09 | 0.47 | 8.09 | 0.57 | 22.13 | 0.03 | 8.11 | 0 | 22.14 | 0.03 |
| 8.37 | 0.7 | 22.4 | 0.1 | 8.4 | 0.2 | 22.44 | 0 | 8.42 | 0 | 22.46 | 0.03 |
| 8.68 | 0.37 | 22.72 | 0.39 | 8.71 | 0.83 | 22.75 | -0.01 | 8.73 | 0 | 22.77 | 0 |
| 8.99 | 0.9 | 23.03 | 0.1 | 9.02 | 0.24 | 23.06 | 0 | 9.04 | 0.54 | 23.09 | 0.14 |
| 9.3 | 0.4 | 23.34 | 0.1 | 9.33 | 0.74 | 23.37 | 0 | 9.35 | 0.2 | 23.39 | 0.05 |
| 9.61 | 0.97 | 23.65 | 0.35 | 9.65 | 0.74 | 23.68 | 0.13 | 9.67 | 0.7 | 23.7 | 0.01 |
| 9.92 | 0.58 | 23.96 | 0.09 | 9.96 | 0.32 | 24 | 0.03 | 9.98 | 0.26 | 24.02 | 0.13 |
| 10.24 | 0.8 | 24.28 | 0.26 | 10.27 | 0.68 | 24.31 | 0 | 10.29 | 0.81 | 24.33 | 0.03 |
| 10.55 | 0.93 | 24.59 | 0.13 | 10.58 | 0.33 | 24.62 | -0.01 | 10.6 | 0.81 | 24.64 | 0 |
| 10.86 | 0.56 | 24.9 | 0.11 | 10.89 | 0.66 | 24.93 | -0.01 | 10.91 | 0.28 | 24.95 | -0.01 |
| 11.17 | 0.56 | 25.21 | 0.21 | 11.21 | 0.38 | 25.24 | -0.01 | 11.23 | 0.74 | 25.26 | -0.01 |
| 11.48 | 1.15 | 25.52 | 0.05 | 11.52 | 0.63 | 25.56 | 0 | 11.54 | 0.3 | 25.58 | -0.01 |
| 11.8 | 0.54 | 25.84 | 0.11 | 11.83 | 0.42 | 25.87 | 0 | 11.85 | 0.76 | 25.89 | 0.16 |
| 12.11 | 1.14 | 26.15 | 0.16 | 12.14 | 0.7 | 26.18 | 0.16 | 12.16 | 0.32 | 26.2 | 0.04 |
| 12.42 | 0.55 | 26.46 | 0.16 | 12.45 | 0.38 | 26.49 | 0.04 | 12.47 | 0.67 | 26.51 | 0 |
| 12.73 | 1.13 | 26.77 | 0.04 | 12.77 | 0.38 | 26.8 | 0 | 12.79 | 0.32 | 26.82 | 0 |
| 13.04 | 0.45 | 27.08 | 0.01 | 13.08 | 0.64 | 27.12 | 0 | 13.1 | 0.76 | 27.14 | -0.01 |
| 13.36 | 1.2 | 27.4 | 0.16 | 13.39 | 0.32 | 27.43 | 0 | 13.41 | 0.31 | 27.45 | -0.01 |
| 13.67 | 0.44 | 27.72 | 0.04 | 13.7 | 0.7 | 27.74 | 0 | 13.72 | 0.31 | 27.76 | 0 |
| 13.98 | 0.44 | 28.02 | 0 | 14.01 | 0.33 | 28.05 | 0 | 14.03 | 0.71 | 28.07 | 0.06 |
| 14.29 | 1.23 | 28.33 | 0 | 14.33 | 0.73 | 28.36 | 0 | 14.35 | 0.32 | 28.38 | 0.06 |
| \-continued | | 28.64 | 0.2 | \-continued | | 28.68 | 0 | \-continued | | 28.7 | 0.06 |

FIG. 3C

WOUND THERAPY SYSTEM WITH FLUID CANISTER VOLUME DETECTION

CROSS-REFERENCE TO RELATED APPLICATIONS

This application claims the benefit of priority to U.S. Provisional Application No. 62/816,704, filed on Mar. 11, 2019 which is incorporated herein by reference in its entirety.

BACKGROUND

The present disclosure relates generally to a wound therapy system, and more particularly to a wound therapy system configured to estimate a volume of a canister that is attached to a negative pressure wound therapy ("NPWT") device.

During operation of a NPWT system, exudates and other fluids from a wound may be collected in a canister detachably mated with the NPWT system. If the canister reaches capacity during therapy, a caregiver may replace the full canister with a new canister. NPWT systems may be used with canisters of different sizes, such as 300 ml, 500 ml, and 1,000 ml. In various situations, it may be desirable to know the volume of the canister that is in fluid communication with the NPWT system. Accordingly, in some NPWT systems, a canister may be provided with one or more markings or other identifiable features representative of the volume of the canister. The canister size is then entered into the NPWT system manually or by electronically scanning marking on the canister.

It may be advantageous to provide a NPWT system configured to estimate a volume of an attached canister without requiring any user input and/or a scanning element.

SUMMARY

According to a first implementation of the present disclosure, a wound therapy system includes a fluid canister, a housing, a pump and a controller. The housing includes a canister receiving attachment to which the canister is releasably secured. The pump is fluidly coupled to the canister and is configured to draw a negative pressure within an interior of the canister. The controller is configured to operate the pump to apply a vacuum to the interior of the canister, obtain one or more measurements representative of a flow of air that is exhausted from the canister interior following the initiation of the operation of the pump and estimate the volume of the canister based on the obtained flow rate measurements.

In some embodiments, the controller is configured to prevent operation of the wound therapy system in response to estimating that the volume of the fluid canister exceeds a predetermined volume corresponding to an upper limit of a quantity of fluid that may be safely evacuated from a patient.

In some embodiments, the controller comprises a memory storing model airflow curves representative of the flow of air that is exhausted from a canister interior during the operation of the wound therapy system with canisters defined by varying volumes.

In some embodiments, the controller is configured to initiate a timer upon initiating operation of the pump. The one or more measurements representative of the flow of air obtained by the controller comprise a flow rate measurement obtained at a predetermined time following the initiation of the operation of the timer. The controller is configured to stop the timer and the operation of the pump in response to the controller obtaining a measurement that the flow of air is below a predetermined flow rate.

In some embodiments, the controller is configured to estimate the volume of the canister by identifying a model airflow curve that is defined by a flow rate at the predetermined time that is substantially similar to the flow rate measurement obtained by the controller. The controller is configured to estimate the volume of the canister by identifying a model airflow curve that is defined by a flow rate that is substantially the same as the predetermined flow rate at a time corresponding to the time interval defined between the initiation of the pump and the stopping of the pump.

In some embodiments, the wound therapy system further includes a wound dressing configured to be sealed about a wound site and a conduit having a first end attached to the wound dressing and a second end attached to a canister inlet. A flow restrictor is positioned between the conduit second end and the canister inlet.

According to one implementation of the present disclosure, a wound therapy system includes a fluid canister, a housing, and a pump. The housing includes a canister receiving attachment to which the canister is releasably secured. The pump is fluidly coupled to the canister and configured to draw a negative pressure within an interior of the canister. The controller is configured to operate the pump to apply a vacuum to the interior of the canister, obtain one or more measurements representative of a pressure within the canister interior following the initiation of the operation of the pump, and estimate the volume of the canister based on the obtained pressure measurements.

In some embodiments, the controller is configured to prevent operation of the wound therapy system in response to estimating that the volume of the fluid canister exceeds a predetermined volume corresponding to an upper limit of a quantity of fluid that may be safely evacuated from a patient. The controller comprises a memory storing model pressure curves representative of the change in pressure within a canister interior during the operation of the wound therapy system with canisters defined by varying volumes. In some embodiments, the controller is configured to initiate a timer upon initiating operation of the pump.

In some embodiments, the one or more measurements representative of pressure within the canister interior are obtained by the controller comprise a pressure measurement obtained at a predetermined time following the initiation of the operation of the timer. The controller may be configured to stop the timer and the operation of the pump in response to the controller obtaining a pressure measurement that corresponds to a predetermined pressure.

In some embodiments, the controller is configured to estimate the volume of the canister by identifying a model pressure curve that is defined by a pressure at the predetermined time that is substantially similar to the pressure measurement obtained by the controller. The controller may be configured to estimate the volume of the canister by identifying a model pressure curve that is defined by a pressure that is substantially the same as the predetermined pressure at a time corresponding to the time interval defined between the initiation of the pump and the stopping of the pump.

In some embodiments, the wound therapy system further includes a wound dressing configured to be sealed about a wound site and a conduit having a first end attached to the wound dressing and a second end attached to a canister inlet. A flow restrictor may be positioned between the conduit second end and the canister inlet.

According to one implementation of the present disclosure, a method of estimating a volume of a canister attached to a negative pressure wound therapy device includes attaching a first canister to a wound therapy device, attaching a conduit between an inlet of the canister and a first wound dressing, operating a pump of the therapy device to attain a desired predetermined negative pressure within a treatment space defined underneath the wound dressing, obtaining one or more measurements of the airflow from an outlet of the canister following the initiation of the pump, obtaining model airflow data curves representative of the change in the rate of airflow from a canister interior during the operation of a wound therapy system with canisters defined by varying volumes, and estimating a volume of the canister using the measured airflow and the obtained model airflow data curves.

In some embodiments, an alert is generated in response to determining that the estimated volume of the canister exceeds a predetermined volume corresponding to an upper limit of a quantity of fluid that may be safely evacuated from a patient.

In some embodiments, a timer is initiated upon initiating operation of the pump. In some embodiments, the airflow measurement is obtained at a predetermined time following the initiation of the operation of the timer. The timer may be stopped in response to the controller obtaining an airflow measurement that is below a predetermined flow rate. The volume of the canister is estimated by identifying a model airflow curve that is defined by a flow rate at the predetermined time that is substantially similar to the flow rate measurement obtained by the controller.

In some embodiments, the volume of the canister is estimated by identifying a model airflow curve that is defined by a flow rate that is substantially the same as the predetermined flow rate at a time corresponding to the time interval defined between the initiation of the pump and the stopping of the pump.

In some embodiments, a volume of the canister is detected using one or more markers or indicators provided on the canister. The detected volume is compared against the estimated volume and an alert is generated if the detected volume and the estimated volume are not substantially the same.

In some embodiments, the first canister is removed from the wound therapy device after the canister volume has been estimated. A second canister is attached to the wound therapy device. A conduit is attached between an inlet of the second canister and a second wound dressing. The pump of the therapy device is operated to attain a desired predetermined negative pressure within a treatment space defined underneath the second wound dressing. One or more measurements of the airflow from an outlet of the second canister following the initiation of the pump are obtained. A volume of the second canister is estimated using the measured airflow and the obtained model airflow data curves. Estimating the volume of the first canister includes making a binary distinction as to whether the canister volume is greater or less than a predetermined volume.

According to one implementation of the present disclosure, a method of estimating a volume of a canister attached to a negative pressure wound therapy device includes attaching a first canister to a wound therapy device, attaching a conduit between an inlet of the canister and a first wound dressing, operating a pump of the therapy device to attain a desired predetermined negative pressure within a treatment space defined underneath the wound dressing, obtaining one or more measurements of pressure within an interior of the canister following the initiation of the pump, obtaining model pressure data curves representative of the change in pressure within the canister interior during the operation of a wound therapy system with canisters defined by varying volumes, and estimating a volume of the canister using the measured pressure and the obtained model pressure data curves.

In some embodiments, an alert is generated in response to determining that the estimated volume of the canister exceeds a predetermined volume corresponding to an upper limit of a quantity of fluid that may be safely evacuated from a patient.

In some embodiments, a timer is initiated upon initiating operation of the pump. In some embodiments, the pressure measurement is obtained at a predetermined time following the initiation of the operation of the timer. The timer is stopped in response to the controller obtaining a pressure measurement that is below a predetermined pressure. In some embodiments, the volume of the canister is estimated by identifying a model pressure curve that is defined by a pressure at the predetermined time that is substantially similar to the pressure measurement obtained by the controller. The volume of the canister may be estimated by identifying a model pressure curve that is defined by a pressure that is substantially the same as the predetermined pressure at a time corresponding to the time interval defined between the initiation of the pump and the stopping of the pump.

In some embodiments, a volume of the canister is detected using one or more markers or indicators provided on the canister. The detected volume is compared against the estimated volume and an alert is generated if the detected volume and the estimated volume are not substantially the same.

In some embodiments, the first canister is removed from the wound therapy device after the canister volume has been estimated. A second canister is attached to the wound therapy device. A conduit is attached between an inlet of the second canister and a second wound dressing. The pump of the therapy device is operated to attain a desired predetermined negative pressure within a treatment space defined underneath the second wound dressing. One or more measurements of the pressure within an interior of the second canister following the initiation of the pump are obtained. A volume of the second canister is estimated using the measured pressure and the obtained model pressure data curves. In some embodiments, estimating a volume of the first canister includes making a binary distinction as to whether the canister volume is greater or less than a predetermined volume.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

FIG. 3B is a table of the pressure measurements on which the model graph of FIG. 3A is based.

FIG. 3C is a table of the flow rate measurements on which the model graph of FIG. 3A is based.

DETAILED DESCRIPTION

Figure 1A:
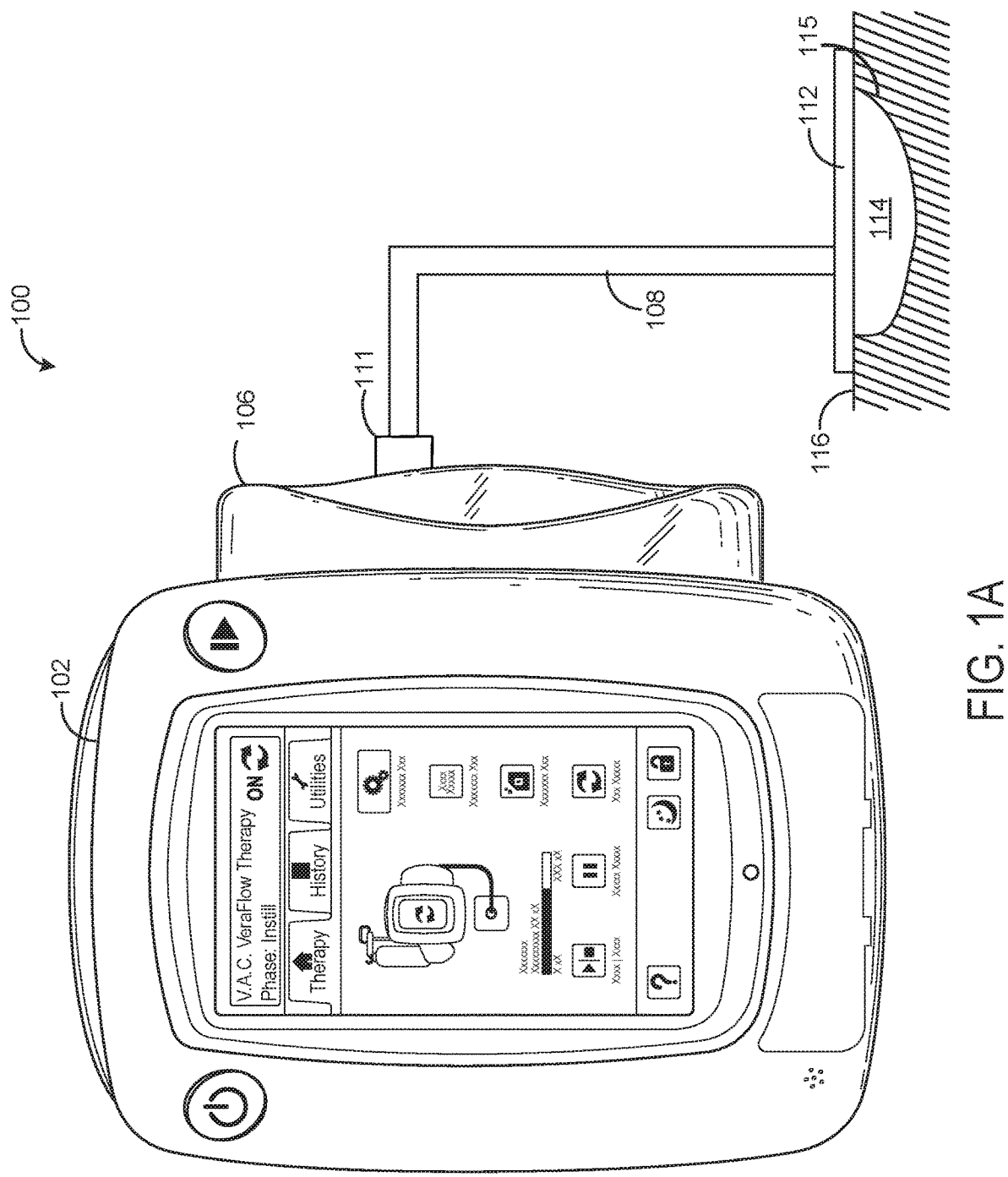
FIG. 1A illustrates a negative pressure wound therapy system attached to a wound, according to an exemplary embodiment.

Referring generally to the FIGURES, a NPWT system and method of its use is shown according to various exemplary embodiments. The NPWT system generally includes a therapy device and a wound dressing. A removed fluid canister is fluidly coupled to each of the therapy device and wound dressing, and is configured to retain fluids (e.g. wound exudate, fluid previously instilled to the wound site during instillation therapy, etc.) removed from the wound site during use of the therapy device. The wound therapy device is configured to accept and be used with fluid canisters of differing volumes.

As will be described in more detail below, the NPWT system is configured to estimate the volume of the fluid canister upon initiation of treatment using the NPWT system by observing one or more parameters such as pressure, flow rate, pump ripple decay, etc. as air is evacuated from a negative pressure circuit defined by the wound treatment space volume defined between the wound dressing and a wound site about which the wound dressing is applied, the fluid canister, and fluid tubing extending between the wound site and the fluid canister. These observed changes are compared against previously obtained model data to estimate the volume of the fluid canister.

Because the volume estimated by the NPWT system using the methods described herein is obtained based on measurements that are based on the physical structure of the canister, the NPWT system may provide a more reliable option via which a volume of a canister may be estimated and/or via which a previously obtained volume may be confirmed, and may avoid or entirely prevent errors that could otherwise occur as a result of a canister marker or other identifier representative of a volume of a canister improperly identifying the volume of the canister. Additionally, the ability of the NPWT system to provide a canister volume estimate without requiring that the canister be provided with markings or other volume identifying elements allows the NPWT system to be used to provide volume estimates irrespective of whether the attached canister includes such markings. Furthermore, because the NPWT system is configured to use measurements obtained during an initial draw down of the negative pressure circuit to estimate volume, the NPWT system requires no additional user input to provide such volume estimates than would otherwise be required to operate the NPWT system.

As noted above, the NPWT system may be used to provide volume estimates independent of any markings provided on a container and intendent of any user input and/or the incorporation of a reader or other scanning element into the NPWT system. However, according to some embodiments, the NPWT system may optionally receive a user input canister volume and/or may include a reader or other scanning element that may be used to read a volume represented by the markings of other volume identifiers provided on a canister that is attached to the therapy device. In such embodiments, the methods and systems described herein may provide the NPWT system with a built in, integrated error-detection system that may alert a user to situations in which there is a discrepancy between the volume estimates.

As will be understood, the canister volume estimated by the NPWT system may be used for any number of purposes, including, e.g. preventing leaks and/or damage to the therapy device; minimizing risks associated with the use of the wound therapy system; monitoring the progress of wound treatment; etc. For example, in some situations the NPWT system may be configured to limit or prevent use of the NPWT system under potentially unsafe conditions during use of the NPWT system in a non-medical setting (e.g., in a home-use setting) or in other situations in which a patient may not be under constant medical supervision. In such situations the NPWT system may be configured to alert a user and/or block operation of the NPWT system in the event that the volume of a canister attached to the therapy device is estimated by the NPWT system to exceed than an upper limit of a quantity of fluid that may be safely evacuated from a wound site. As such, the NPWT system may prevent a situation in which the use of a large canister with the therapy device would otherwise allow the NPWT system to continue operating to withdraw fluid from the wound site even after this threshold quantity had been exceeded.

Wound Therapy System

Figure 1B:
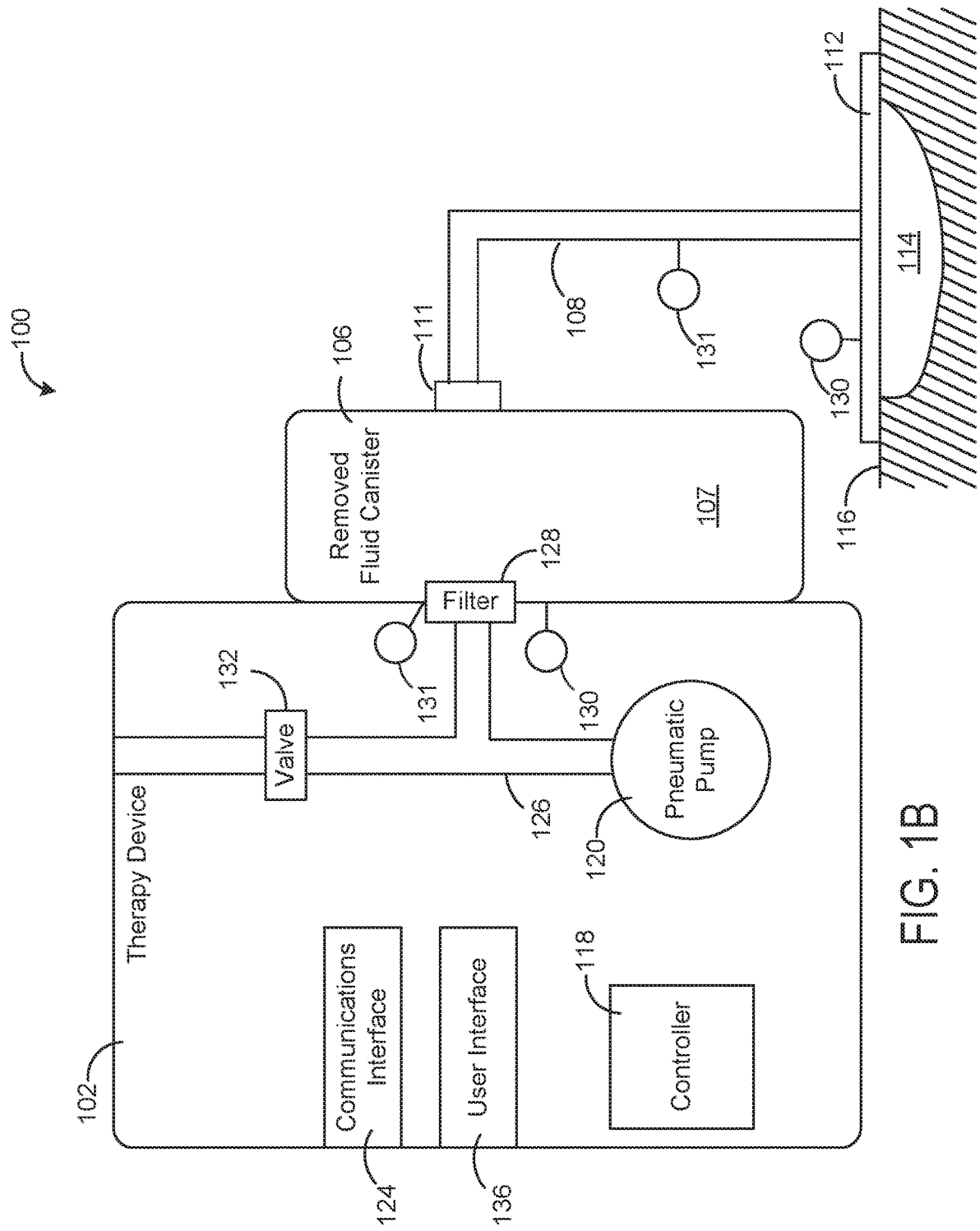
FIG. 1B is a block diagram of the negative pressure wound therapy system of FIG. 1A, according to an exemplary embodiment.

Referring to FIGS. 1A and 1B, a negative pressure wound therapy (NPWT) system 100 is shown according to an exemplary embodiment. NPWT system 100 is shown to include a therapy device 102 fluidly connected to a wound dressing 112 via a conduit 108. Wound dressing 112 may be adhered or sealed to a patient's skin 116 surrounding a wound 115 to define a treatment space 114. Several examples of wound dressings 112 which can be used in combination with NPWT system 100 are described in detail in U.S. Pat. No. 7,651,484 granted Jan. 26, 2010. U.S. Pat. No. 8,394,081 granted Mar. 12, 2013, U.S. patent application Ser. No. 14/087,418 filed Nov. 22, 2013, and U.S. Provisional Patent Application No. 62/650,132 filed Mar. 29, 2018. The entire disclosure of each of these patents and patent applications is incorporated by reference herein.

Therapy device 102 can be configured to provide negative pressure wound therapy by reducing the pressure within the treatment space 114. Therapy device 102 can draw a vacuum within the treatment space 114 (relative to atmospheric pressure) by removing fluids such as wound exudate, air, and other fluids from the wound 115. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound 115 may include instillation fluid previously delivered to wound 115. Instillation fluid can include, for example, a cleansing fluid, a prescribed fluid, a medicated fluid, an antibiotic fluid, or any other type of fluid which can be delivered to wound 115 during wound treatment. In some embodiments, therapy device 102 is configured to deliver instillation fluid to wound 115, as described in U.S. Provisional Patent Application No. 62/650,132 filed Mar. 29, 2018, the entire disclosure of which is incorporated by reference herein.

Fluids removed from wound 115 pass through conduit 108 and are collected in a removed fluid canister 106. Conduit 108 may have a first end coupled to an inlet of the canister 106 and a second end fluidly coupled to the wound treatment space 114 via the wound dressing 112. As will be described in more detail below, according to some embodiments, a restriction element 111 may be provided between the opening 109 of the canister 106 and the first end of the conduit 108 and/or elsewhere along the conduit 108. According to some embodiments, the restriction element 111 may define a fixed size opening that is smaller than an opening defined by the inlet of the canister 106 and/or the inlet of the first end of the conduit 108. In other embodiments, the size of the opening defined by the restriction element 111 may be varied manually and/or automatically as desired.

The canister 106 is configured to collect wound exudate and other fluids removed from wound 115. The canister 106 is detachable from therapy device 102 to allow canister 106 to be emptied and replaced as needed. The canister 106 may be defined by any desired volume, with canisters 106 of differing volumes interchangeably being configured to be attached to and used with the therapy device 102.

In various embodiments, the canister 106 may optionally include one or more markings or other identifiable features via which a user and/or the therapy device 102 may determine the volume of the canister 106. For example, in some embodiments, the therapy device 102 may optionally include a scanner or other reader configured to read a marking or readable structure provided on or associated with the canister 106. According to other embodiments, the canister 106 may optionally be formed without any markings or other identifiable features indicative of a size or volume of the canister 106.

Referring to FIG. 1B, a block diagram illustrating the therapy device 102 in greater detail is shown according to an exemplary embodiment. As illustrated by FIG. 1B, therapy device 102 includes a pneumatic pump 120, and may also optionally include a relief valve 132, a filter 128, and a controller 118. Pump 120 can be fluidly coupled to canister 106 (e.g., via conduit 126) and can be configured to draw a vacuum within canister 106 by pumping air out of canister 106. In some embodiments, pump 120 is configured to operate in both a forward direction and a reverse direction. For example, pump 120 can operate in the forward direction to pump air out of canister 106 and decrease the pressure within canister 106. Pump 120 can operate in the reverse direction to pump air into canister 106 and increase the pressure within canister 106 and/or to instill fluid to the wound 115. Pump 120 can be controlled by controller 118, described in greater detail below.

Filter 128 can be positioned between canister 106 and pump 120 (e.g., along conduit 126) such that the air pumped out of canister 106 passes through filter 128. Filter 128 can be configured to prevent liquid or solid particles from entering conduit 126 and reaching pump 120. Filter 128 may include, for example, a bacterial filter that is hydrophobic and/or lipophilic such that aqueous and/or oily liquids will bead on the surface of filter 128. Pump 120 can be configured to provide sufficient airflow through filter 128 such that the pressure drop across filter 128 is not substantial (e.g., such that the pressure drop will not substantially interfere with the application of negative pressure to the wound treatment space 114).

Valve 132 can be fluidly connected with pump 120 and filter 128 via conduit 126. In some embodiments, valve 132 is configured to control airflow between conduit 126 and the environment around therapy device 102. For example, valve 132 can be opened to allow airflow into conduit 126, and closed to prevent airflow into conduit 126. Valve 132 can be opened and closed by controller 118. The negative pressure circuit may include any component of the NPWT system 100 that can be maintained at a negative pressure when performing negative pressure wound therapy (e.g., conduit 126, canister 106, conduit 108, and/or wound treatment space 114).

In some embodiments, therapy device 102 includes one or more sensors. For example, therapy device 102 is shown to include one or more pressure sensors 130 configured to measure the pressure within canister 106 and/or the pressure within the wound treatment space 114. Pressure measurements recorded by pressure sensor 130 can be communicated to controller 118. According to various embodiments, the controller 118 may use the pressure measurements from pressure sensor(s) 130 to maintain the wound 115 at a desired negative pressure. For example, controller 118 can activate pump 120 in response to a pressure measurement from pressure sensor 130 exceeding a negative pressure setpoint in order to reduce the pressure at wound 115. In various embodiments, the therapy device 102 may additionally, or alternatively, include one or more flow rate sensors 131 configured to measure a rate of airflow into and/or out from the fluid canister 106 and/or conduit 108.

Controller

Figure 2:
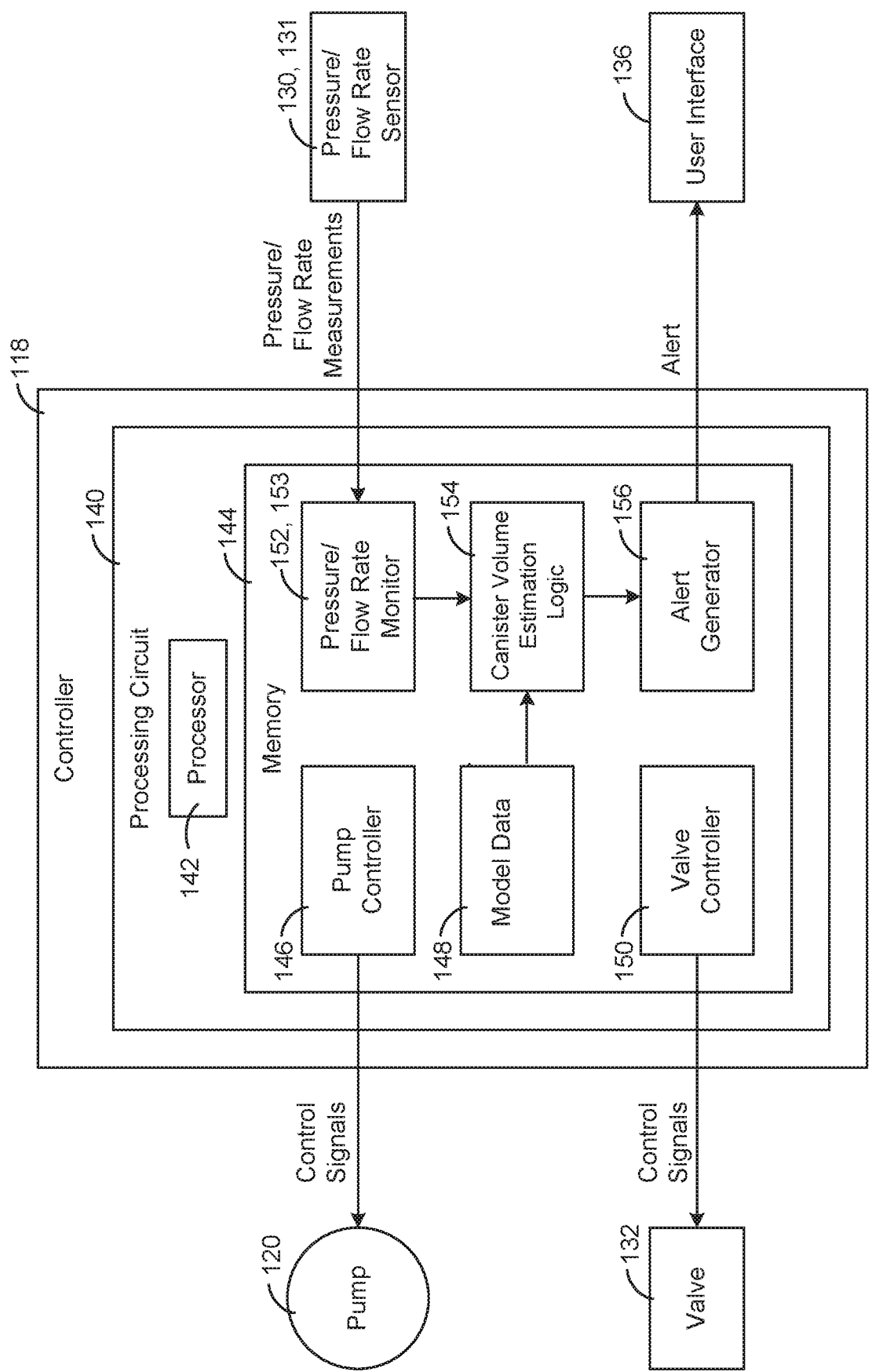
FIG. 2 is a block diagram of the controller of the negative pressure wound therapy system of FIG. 1A, according to an exemplary embodiment.

Referring to FIG. 2, controller 118 is shown to include a processor 142 and memory 144. Processor 142 may be a general purpose or specific purpose processor, an application specific integrated circuit (ASIC), one or more field programmable gate arrays (FPGAs), a group of processing components, or other suitable processing components. Processor 142 is configured to execute computer code or instructions stored in memory 144 or received from other computer readable media (e.g., CDROM, network storage, a remote server, etc.). According to various embodiments, the processor 142 is configured to operate the controller to automatically estimate the volume of a canister 106 that is attached to the therapy device 102.

Memory 144 may include one or more devices (e.g., memory units, memory devices, storage devices, etc.) for storing data and/or computer code for completing and/or facilitating the various processes described in the present disclosure. Memory 144 may include random access memory (RAM), read-only memory (ROM), hard drive storage, temporary storage, non-volatile memory, flash memory, optical memory, or any other suitable memory for storing software objects and/or computer instructions.

Memory 144 may include database components, object code components, script components, or any other type of information structure for supporting the various activities and information structures described in the present disclosure. Memory 144 may be communicably connected to processor 142 and may include computer code for executing (e.g., by processor 142) one or more processes described herein. When processor 142 executes instructions stored in memory 144, processor 142 generally configures controller 118 to complete such activities.

According to various embodiments, the memory 144 is configured to store canister volume estimation logic 154, which, when executed, is configured use stored model data 148 and pressure data obtained using pressure sensor 130, flow rata data obtained using flow rate sensor 131 and/or pump ripple data to estimate a volume of the canister 106 that is attached to the therapy device 102. In some embodiments in which an optionally provided flow restriction element 111 is defined by an actuatable element, the canister volume estimation logic 154 may optionally additionally be configured to vary the opening defined by the restriction element 111, such as, e.g., by narrowing the opening of the restriction element 111 during the drawdown of the negative pressure circuit.

Controller 118 is shown to include a pump controller 146. Pump controller 146 can be configured to operate pump 120 by generating and providing control signals to pump 120. The control signals provided to pump 120 can cause pump 120 to activate, deactivate, or achieve a variable capacity or speed (e.g., operate at half speed, operate at full speed, etc.).

In some embodiments, pump controller 146 may receive input from an optionally provided canister sensor configured to detect whether canister 106 is present. Pump controller 146 can be configured to activate pump 120 only when canister 106 is present. For example, pump controller 146 can check whether canister 106 is present and can activate pump 120 in response to a determination that canister 106 is present. However, if canister 106 is not present, pump controller 146 may prevent pump 120 from activating.

Controller 118 is shown to include a pressure monitor 152. Pressure monitor 152 can be configured to monitor the pressure within canister 106 and/or the pressure within the wound treatment space 114 using feedback from pressure sensor 130. For example, pressure sensor 130 may provide pressure measurements to pressure monitor 152. Pressure monitor 152 can use the pressure measurements to determine the pressure within canister 106 and/or the pressure within wound dressing 112 or wound treatment space 114 in real-time. As will be understood, according to various embodiments, the pressure measurement values relied upon in estimating the volume of the fluid canister 106 by the canister volume estimation circuit 154 may be pressure measurements provided by the pressure monitor 152.

The controller 118 may also include a flow rate monitor 153. Flow rate monitor 153 can be configured to monitor the flow rate of air into and/or out from the canister 106 a using feedback from flow rate sensor 131. For example, flow rate sensor 131 may provide flow rate measurements to flow rate monitor 155. Flow rate monitor 153 can use the pressure measurements to determine the rate of flow into and/or out from the canister 106 in real-time. As will be understood, according to various embodiments, the flow rate measurement values relied upon in estimating the volume of the fluid canister 106 by the canister volume estimation circuit 154 may be flow rate measurements provided by the flow rate monitor 153.

In some embodiments, therapy device 102 includes a data communications interface 124 (e.g., a USB port, a wireless transceiver, etc.) configured to receive and transmit data. Communications interface 124 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 124 can include a USB port or an Ethernet card and port for sending and receiving data via an Ethernet-based communications link or network. In another example, communications interface 124 can include a Wi-Fi transceiver for communicating via a wireless communications network or cellular or mobile phone communications transceivers.

In some embodiments, therapy device 102 includes a user interface 136. User interface 136 may include one or more buttons, dials, sliders, keys, or other input devices configured to receive input from a user. User interface 136 may also include one or more display devices (e.g., LEDs, LCD displays, etc.), speakers, tactile feedback devices, or other output devices configured to provide information to a user. In some embodiments, the pressure measurements recorded by pressure sensor 130 and/or flow rate measurements records by the flow rate sensor 131 are presented to a user via user interface 136. User interface 136 can also display alerts generated by controller 118.

Operation of NPWT System

Following the application of a wound dressing 112 to the skin 116 surrounding a wound 115. NPWT treatment is initiated using the NPWT system 100 by closing valve 132 (if included) and operating pump 120 to draw a vacuum within the negative pressure circuit defined by the canister 106, tubing 108 and wound treatment space 114 defined between the wound 115 and the wound dressing 112. The operation of the pump 120 is continued until a desired negative pressure has been attained within the treatment space 114 as, e.g., determined by monitoring pressure using pressure sensor(s) 130), at which point operation of the pump 120 may be ceased. As will be described in more detail below, according to various embodiments, the NPWT system 100 is configured to estimate a volume of the canister 106 attached to (either directly, or via tubing) the therapy device 102 using pressure, flow rate, and/or pump ripple measurement obtained during the initial draw-down of the negative pressure circuit. Following the attainment of the desired negative pressure at the wound space 114, NPWT treatment using the NPWT system 100 may continue according to any number of desired treatment protocols.

Figure 3A:
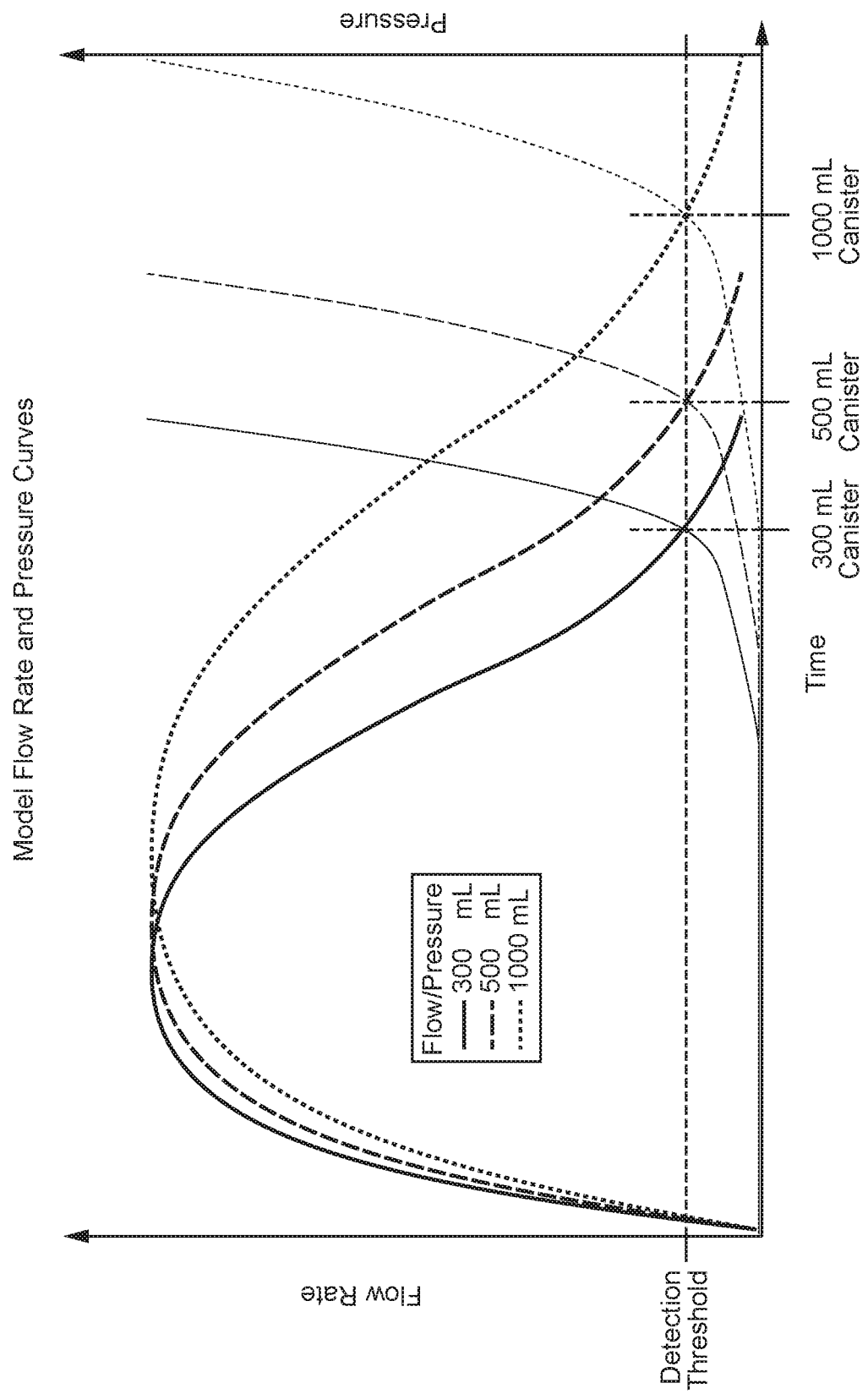
FIG. 3A is a model graph representative of changes in pressure and flow rate during an initial draw down of negative pressure wound therapy devices having fluid canisters of differing volumes, according to an exemplary embodiment.

Referring to FIG. 3A, a model graph representative of changes in pressure and flow rate during operation of NPWT systems 100 having varying sized canisters 106 operated under similar operating conditions is shown according to one embodiment. Given the large volume defined by the interior of the fluid canister 106 and the substantial lack of resistance to the flow of air out of the canister 106 (apart from the minimal resistance encountered as air flows through optionally provided filter 128), the pump 120 operates under substantially free flow conditions during an initial phase of the draw down process during which air is being evacuated from the interior of the canister 106. However, once all (or substantially all of) the initial volume of air within the canister 106 has been evacuated, and as air begins to be evacuated from the conduit 108 and wound treatment space 114, the increased flow resistance encountered as air flows through the narrow tubing 106 results in a measurable decrease of the rate of change of flow of air that is evacuated from the negative pressure circuit.

As noted above, according to some embodiments, a restriction element 111 configured to further narrow and restrict the flow of air being evacuated from the negative pressure circuit may optionally be incorporated between the canister 106 and the conduit 108. By further increasing the resistance to the flow of air from the conduit 108 and wound treatment space 114, the rate of airflow may be further reduced, resulting in an even more marked and pronounced changed in the measured flow which, which may facilitate the identification of the inflection point in the flow rate curve representative of the time at which all of (or substantially all of) the air in the canister 106 has been evacuated. As illustrated by FIG. 3A, given the larger volume defined by (and thus greater amount of air contained within) large canisters, the time interval between the initiation of the pump 120 and the occurrence of the inflection point in the flow rate curve will be greater for large canisters 106 than for smaller canisters 106.

As also illustrated by the graph of FIG. 3A, during the initial, substantial free flow of air immediately following the initiation of pump 120, pressure within the fluid canister 106 remains unchanged, or substantially unchanged. Negative pressure within the canister 106 slowly begins to increase as air continues to be evacuated from the canister 106 interior following the initiation of pump 120. However, as illustrated by FIG. 3A, given the relatively large volume of the canister 106 interior (as compared to the remaining volume of the negative pressure circuit), negative pressure within the canister 106 does not measurably begin increasing until air has been entirely (or substantially entirely) evacuated from the canister 106, at which point a marked and notable increase of the negative pressure within the canister 106 occurs. As illustrated by FIG. 3A, given the longer time required to evacuate all (or substantially all) of the air within larger canisters, the inflection point in the pressure curve (representative of the marked increase in pressure occurring upon all, or substantially all, of the air within the canister being evacuated) for a larger container will occur at the later time than the time associated with the inflection point in the pressure curve of smaller canisters 106.

The NPWT system 100 is configured to utilize the notable and distinguishable inflection points associated with the changing pressure within a canister and the change in the rate of air being evacuated from the negative pressure circuit occurring in response to the evacuation of all (or substantially all) of the air from within a canister, and the variation in the time following initiation of the pump 120 at which these inflection points occur for canisters of differing volumes, to estimate the volume of a canister 106 that is attached to the therapy device 102. According to various embodiments, measurements of pump ripple-reflective of the changes in the pump operation that occur between the evacuation of air from the canister 106 and the evacuation of air from the remainder of the negative pressure circuit—may also by obtained and used by the NPWT system 100 to estimate canister volume 100.

In particular, as illustrated by the representative pressure and flow rate data of FIGS. 3B and 3C, according to various embodiments, the NPWT system 100 may be configured to obtain pressure, flow rate and/or pump ripple decay measurements representative of the operation of the NPWT system 100 with canisters of varying volumes and under a variety of different operating conditions (e.g. differing target pressures, differing initial pressure within the negative pressure circuit, relative humidity, differing volumes defined by the conduit 108 and wound treatment space, differing pumps, etc.). For example, the pressure and flow rate data of FIGS. 3B and 3C is representative of the operation of one embodiment of a NPWT system 100 with 300 mL. 500 mL and 1000 mL containers under temperature conditions of approximately 25.2° C. and a relative humidity of approximately 49.8%. Graphs representative of the pressure and flow rate data of FIG. 3B and FIG. 3C are provided in FIGS. 3D and 3E, respectively.

Figure 3D:
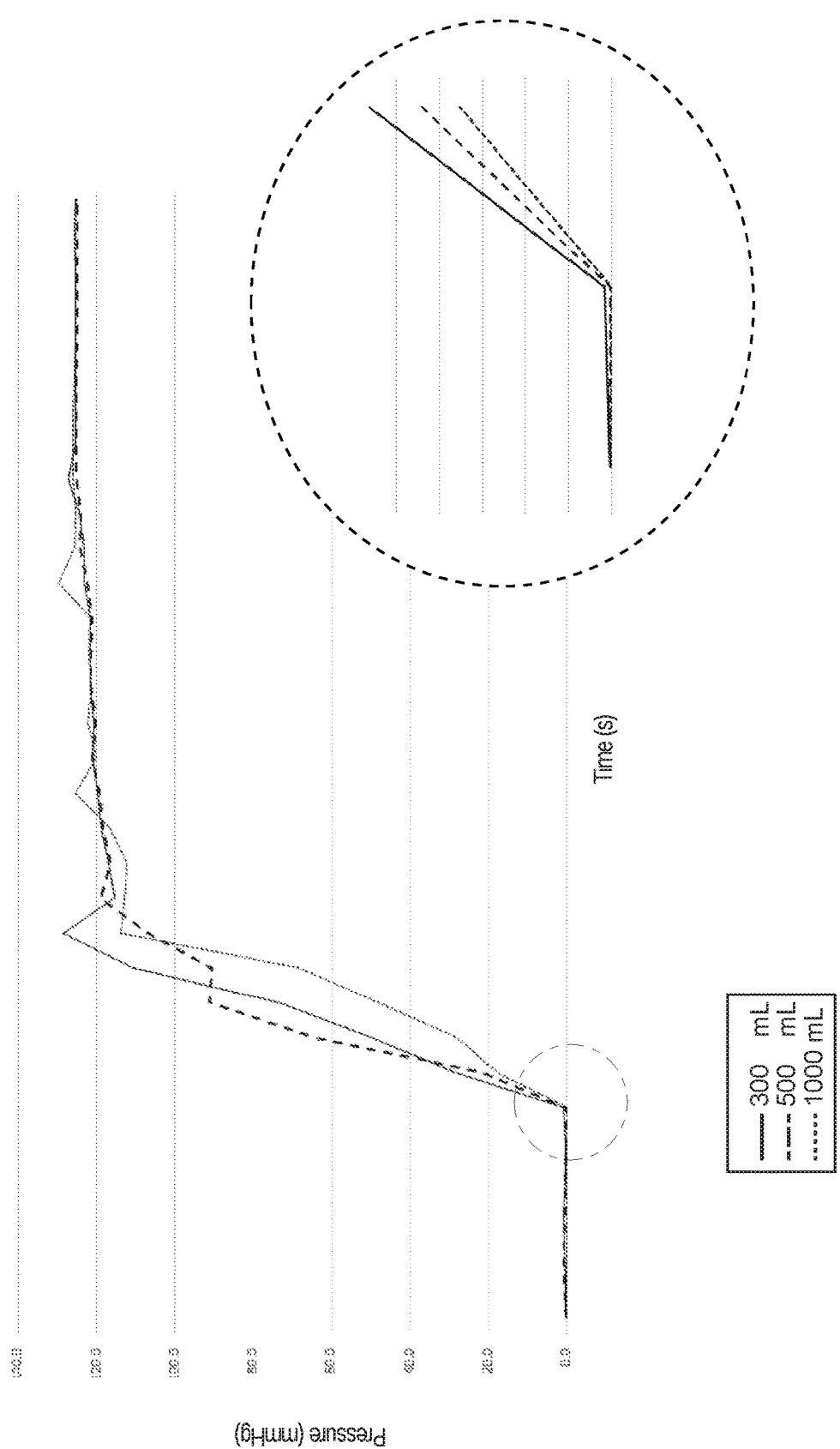
FIG. 3D is a graph representative of the pressure measurement values of the table of FIG. 3B.
Figure 3E:
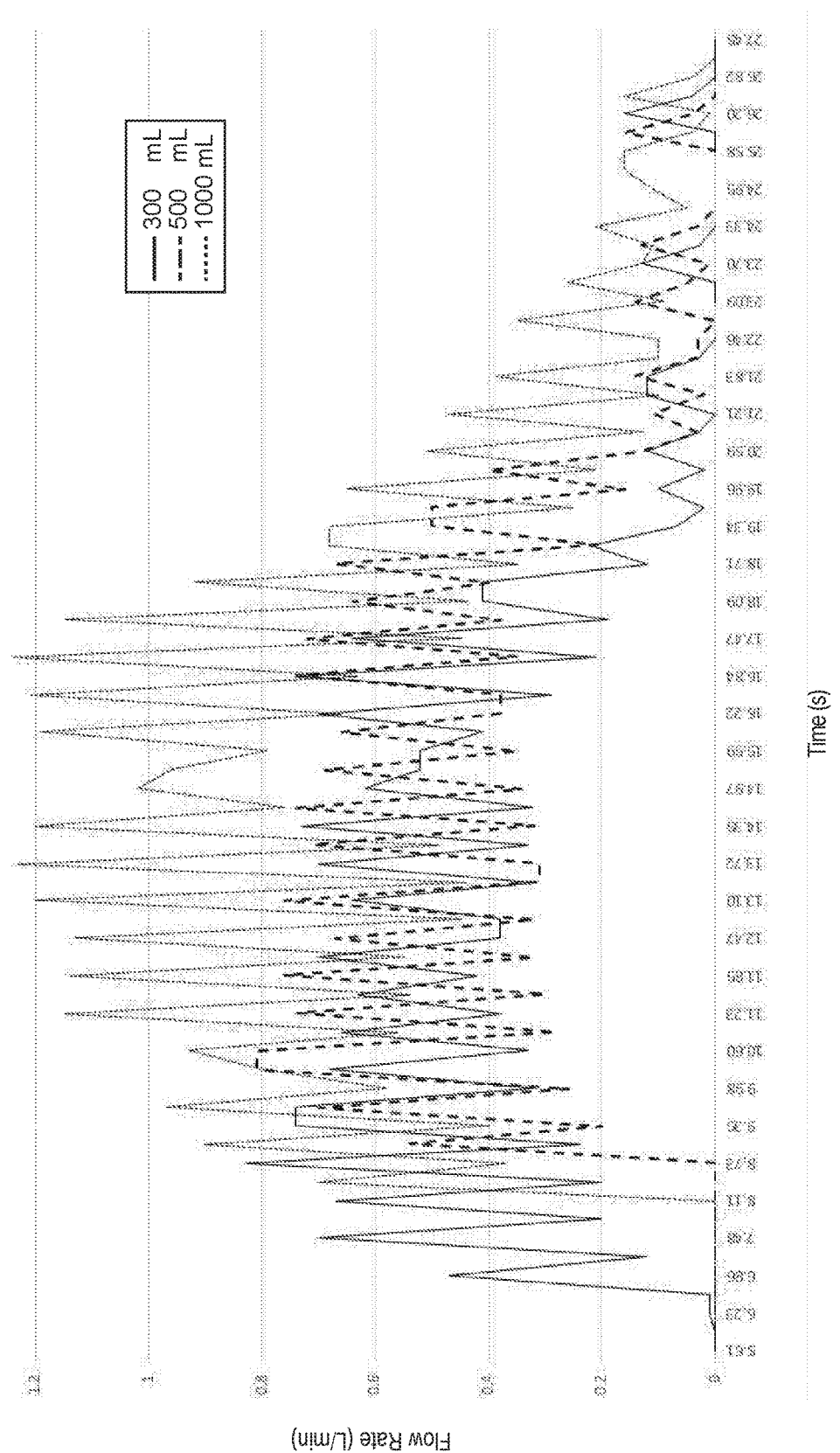
FIG. 3E is a graph representative of the flow rate measurement values of the table of FIG. 3C.

As illustrated by the graphs of FIGS. 3D and 3E, the pressure and flow rate data obtained by the NPWT system 100 may exhibit noise owing to any number of different factors, including. e.g. pump ripple. Accordingly, in various embodiments, any number of, or combination of various function approximators, statistical methods, machine learning systems, model generators, etc. may optionally be used to smooth, curve fit, or otherwise process the data to generate model decay curves, such as, e.g., the model decay curves representatively illustrated by the embodiment of the model graph of FIG. 3A.

As illustrated by the model graph of FIG. 3A, although canisters 106 of differing volumes exhibit different changes in pressure, flow rate and pump ripple (not shown) over time, during certain intervals during the draw down process, such as, e.g., immediately following the initiation of the pump and/or once the target negative pressure has been substantially attained, the differences between the curves of varying sized canisters may be more difficult to accurately distinguish. Accordingly, in various embodiments, in addition to obtaining pressure, flow rate and/or pump ripple decay curves for NPWT systems operated with different sized canisters 106 and/or under varying condition, the NPWT system 100 may be configured to identify relevant ranges and/values of flow rate, pressure, ripple decay and/or time that correspond to the inflection points in the flow rate pressure and ripple decay curves against which time, pressure, flow and/or pressure measurements obtained during operation of the NPWT system 100 may be applied to facilitate and increase the accuracy of the estimate of the volume of the canister 106 attached to the therapy device 102.

For example in embodiments in which the NPWT system 100 is configured to estimate a volume based on one or more parameter measurements obtained following the expiration of a timers (such as, e.g., the method of FIG. 6 and/or the method of FIG. 10) the time interval selected for the timer may be selected to correspond to a time range having a lower limit equal to the time at which—according to the model data—an inflection in pressure, flow rate and/or pump ripple is expected to occur for a volume corresponding to the smallest anticipated canister 106 volume that would be expected to be used with the NPWT system 100 and an upper limit equal to the time at which—also according to the model date—an inflection in pressure, flow rate and/or pump ripple is expected to occur for a volume corresponding to the largest anticipated canister 106 volume that would be expected to be used with the NPWT system 100.

Given the marked increase in negative pressure that occurs upon evacuation of the air from the canister 106 during a drawdown of the negative pressure circuit, according to embodiments in which the attainment of a predetermined pressure measurement is used by the NPWT system 100 to estimate canister 106 volume (such as, e.g. in the method of FIG. 6), the pressure value selected as the predetermined pressure value may be selected to be between approximately 20% of the pressure at the inflection point on the pressure decay curve.

Similarly, given the marked decrease in the change in the rate of airflow from the negative pressure that occurs upon evacuation of the air from the canister 106 during a drawdown of the negative pressure circuit, according to embodiments in which the attainment of a predetermined flow rate is used by the NPWT system 100 to estimate canister 106 volume (such as, e.g. in the method of FIG. 6), the flow rate value selected as the predetermined flow rate value may be selected to be between approximately ±20% of the flow rate at the inflection point on the pressure decay curve. For example, in some embodiments, the predetermined flow rate may be between approximately 0.5 L/min and approximately 0.05 L/min. and more specifically, between approximately 0.3 L/min and approximately 0.1 L/min.

Figure 4:
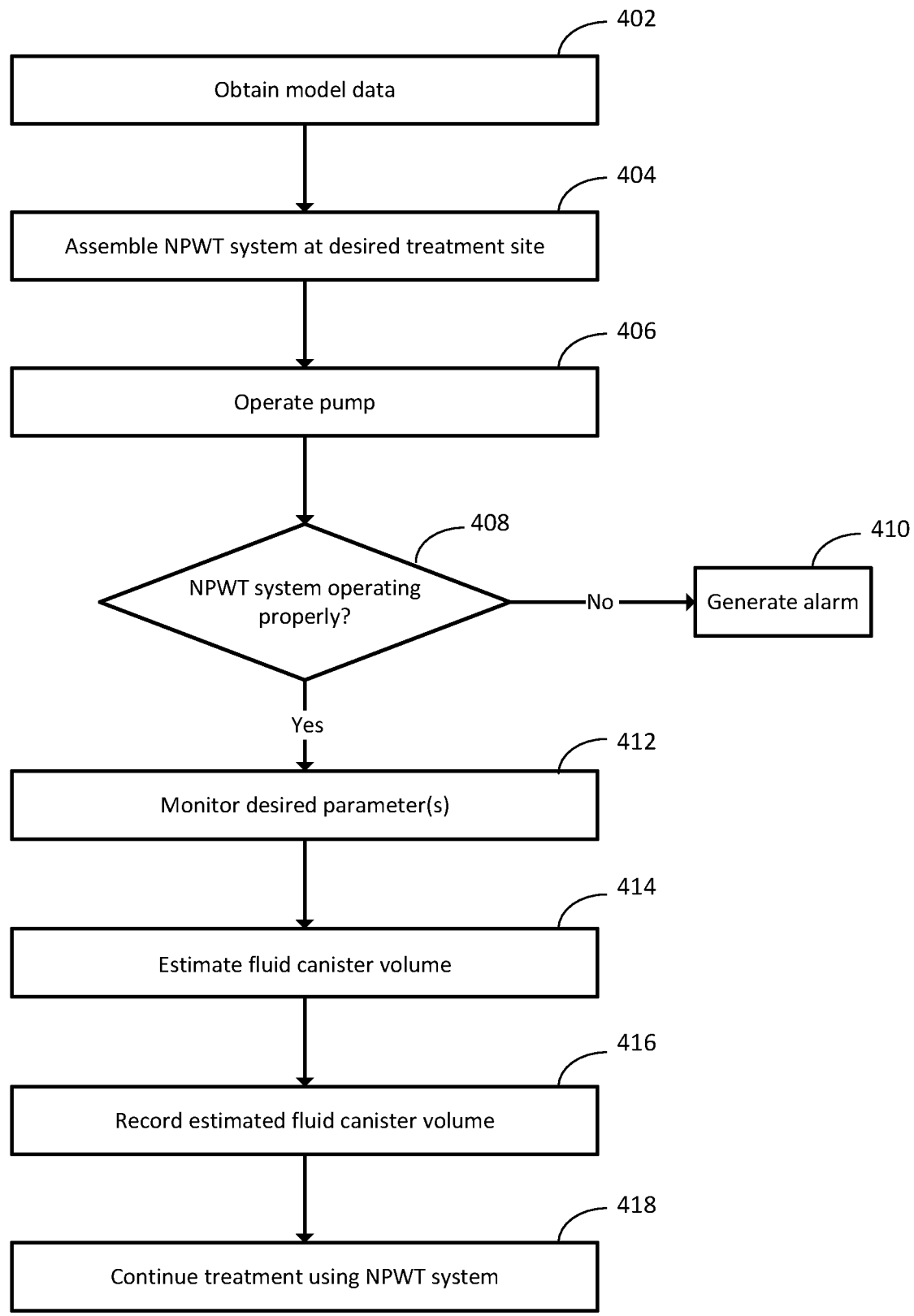
FIG. 4 is a flowchart of a method of operating a negative pressure wound therapy system, according to an exemplary embodiment.

Referring to FIGS. 4-10, flowcharts of various methods for operating the NPWT system 100 are shown according to various embodiments. Shown in FIG. 4 is a representative embodiment of a method of providing NPWT treatment using the NPWT system 100 according to one embodiment. At step 402, model data representative of changes in pressure, flow rate and/or pump ripple over time during an initial draw down of a negative pressure circuit under a variety of clinically relevant conditions and states (e.g. fluid canister volume, wound treatment space volumes, conduit volumes, dressing/foam characteristics, initial pressure within the negative pressure circuit, target negative pressure, etc.) is obtained from any desired source.

In some embodiments, the model data obtained at step 402 may comprise accessing model data 148 previously obtained and stored in the control 118 memory 144. According to other embodiments, such model data may be generated using any number of, or combination of various function approximators, statistical method, machine learning systems, etc. The model data obtained at step 402 may include any number of different pressure decay curves, flow rate curves, pump ripple curves, functions, lookup tables, etc., and may be obtained as pre-existing information that is input and stored by the controller, and/or may be obtained and processed by the controller 118 during an optional, initial training procedure conducted by the controller 118 prior to the use of the NPWT system 100 to treat wound site 114. For example, according to some embodiments, step 402 of obtaining model data may be performed as part of the assembly of the NPWT system 100 at the desired treatment site of step 404. Non-limiting examples of various exemplary training procedures by which such relationships may be generated by the controller 118 are outlined in related, U.S. Provisional Application 62/650,132, filed Apr. 17, 2018 and titled WOUND THERAPY SYSTEM WITH WOUND VOLUME ESTIMATION, the entire disclosure of which is incorporated by reference herein.

At step 404, wound dressing 112 is applied to the patient's skin 116 surrounding a wound 115, and the wound dressing 112 is fluidly connected to a fluid canister 106 that is attached to a therapy device 102. Once the NPWT system 100 has been assembled, at step 406, the pump 120 is operated to draw a vacuum in the negative pressure circuit.

According to various embodiments, at step 408, the NPWT system 100 may optionally be configured to confirm that an initial free flow of air following the initiation of the pump 120 is attributable to the evacuation of air from the fluid canister 106—as opposed to a problem in the NPWT system 100. For example, according to some embodiments, the NPWT system 100 may be configured to differentiate the initial free flow of evacuated air from a gross leak resulting from the canister 106 being improperly attached to, or entirely omitted from, the therapy device 102 via the incorporation of one or more sensors or other elements configured to detect the attachment of the canister 106 to the therapy device 102.

Although the initial evacuation of air from the negative pressure circuit is characterized by an initial free flow of air, under proper operating conditions, the flow of evacuated air from the negative pressure circuit gradually decreases as air from the canister 106 is emptied. In contrast, in the event of a leak in the tubing 106 and/or an improper seal of the wound dressing 112, the flow of evacuated air from the negative pressure circuit may continue to flow for an extended period of time under free flow, or almost free conditions following the initial operation of the pump 120. Accordingly, in some embodiments, at step 408, the NPWT system 100 may additionally, or alternatively be optionally configured alert a user and/or terminate operation of the NPWT system 100 at step 410 in the event that such a leak in the negative pressure circuit is detected.

As will be discussed in more detail with reference to FIGS. 5-7, 9 and FIG. 10, at step 412, as air is evacuated from the negative pressure circuit during operation of the pump 120, at least one of a flow rate of the air from the negative pressure circuit, a pressure within the interior of the canister 106 and/or a pump ripple is monitored. At step 414, the measurements obtained from monitoring the one or more parameters during step 412 and the model data obtained at step 402 are used by the controller 118 to estimate the volume of the fluid canister 106. This estimated volume may optionally be recorded at step 416 for future use by the wound therapy system 416. At step 418, treatment using the NPWT system 100 may be continued according to any number of various protocols.

Figure 5:
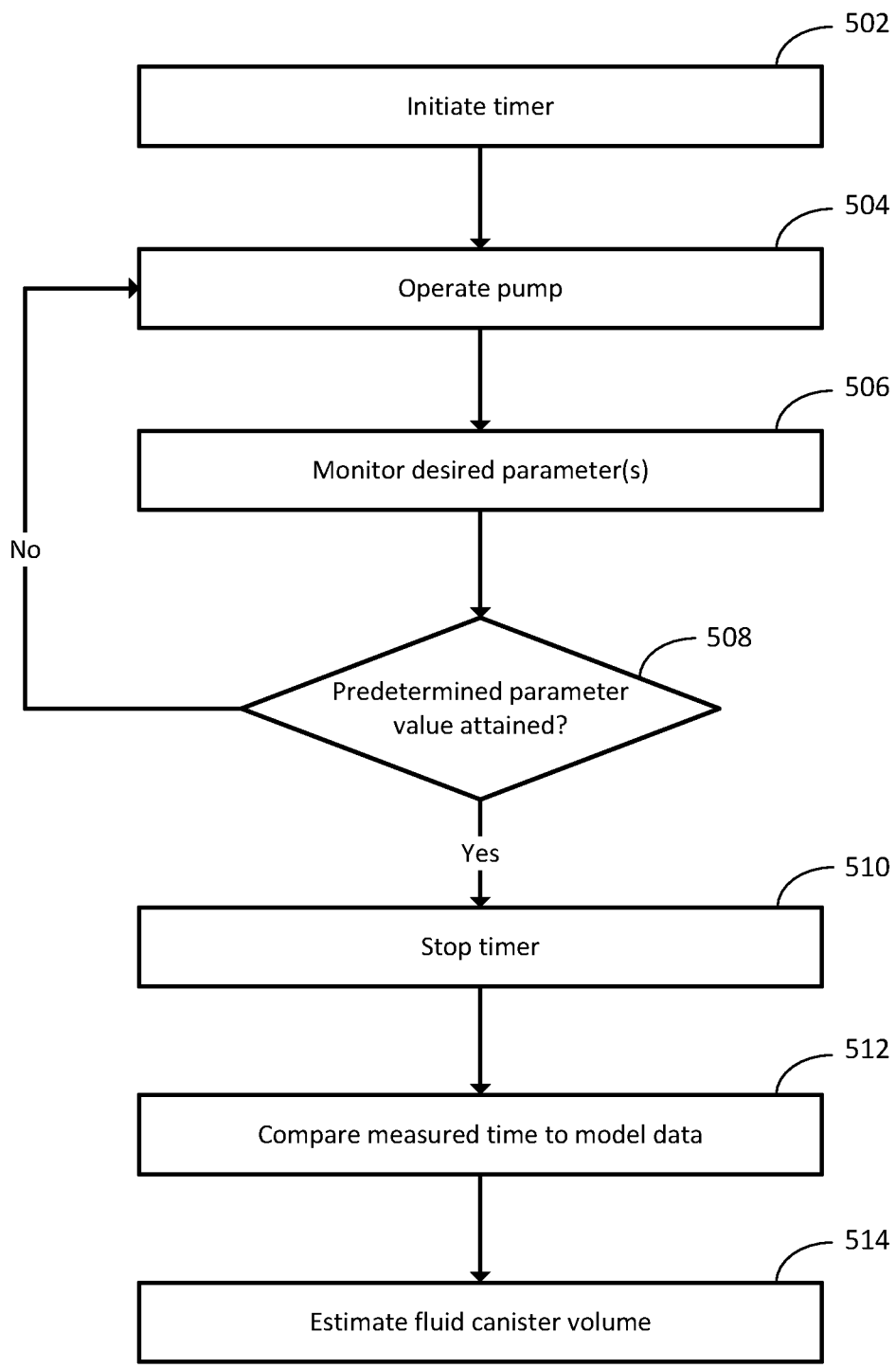
FIG. 5 is a flowchart of a method for estimating a fluid canister volume, according to an exemplary embodiment.

Referring to FIG. 5, a method of estimating a volume of a canister 106 using the NPWT system 100 is shown according to one embodiment. As shown in FIG. 5, at step 502, a timer is initiated to mark the start of the operation of the pump 120 at step 504. Following the initiation of the timer, one or more of the: air flowing out from the negative pressure circuit, the pressure within the canister 106 and/or pump ripple is monitored at step 506. As represented by step 508, the one or more parameters are monitored until the monitored parameter has attained a predetermined value, at which point, at step 510, the timer is stopped. At step 512, the predetermined parameter value and the time that was required to attain the determined parameter value as measured at step 510 are compared to the model data previously obtained by the NPWT system 100 (such as, e.g. model data 148 stored in the memory 144) representative of flow rate, pressure and/or pump ripple decay during operation of NPWT systems having varying sized canister volumes under operating conditions similar to those during step 502-510. At step 514, the volume of the canister 106 is estimated based on the identification of a model data set exhibiting a flow rate, pressure and/or pump ripple value reading corresponding to the predetermined value used in step 508 at a time corresponding substantially to the time interval measured at step 510.

Figure 6:
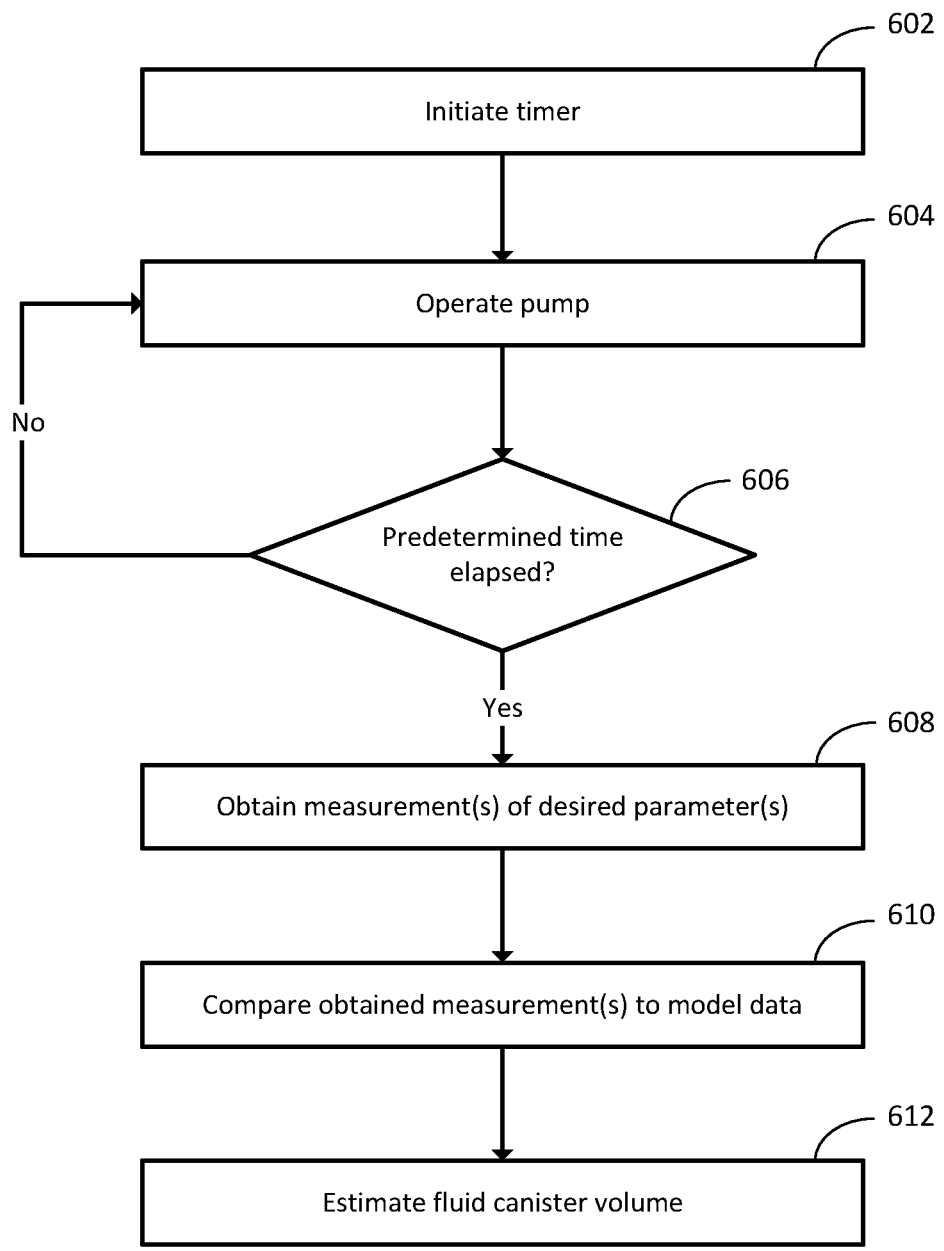
FIG. 6 is a flowchart of a method for estimating a fluid canister volume, according to an exemplary embodiment.

Referring to FIG. 6, a method of estimating the volume of a canister 106 is shown according to another embodiment. As shown in FIG. 6, at step 602, a timer is set for a predetermined time. Upon setting the timer at step 602, operation of the pump 120 is initiated at step 604. According to various embodiments, the predetermined time interval set at step 602 may be selected to correspond to a time that is approximately equal to an estimated time that would be required to evacuate air from within the interior of the smallest size canister with which the NPWT system 100 would be expected to be used. Operation of the pump 120 is continued until the time interval set at step 602 has been determined to have expired at step 606.

Upon expiration of the time interval at step 606, at step 608, a measurement of at least one or more of the flow rate of air being evacuated from the negative pressure circuit, the pressure in the canister 106 and/or pump ripple is obtained, (e.g., using flow rate sensor(s) 131 and/or pressure sensor(s) 130). At step 610, the time interval set at step 602 and the parameter measurement obtained at step 608 are compared to the model data previously obtained by the NPWT system 100 (such as, e.g. model data 148 stored in the memory 144) representative of flow rate, pressure and/or pump ripple decay during operation of NPWT systems having varying sized canister volumes under operating conditions similar to those during step 602-608. At step 612, the volume of the canister 106 is estimated based on the identification of a model data set exhibiting a flow rate, pressure and/or pump ripple value reading corresponding to the parameter measurement obtained at step 608 at a time corresponding to the time interval set at step 602.

Figure 7:
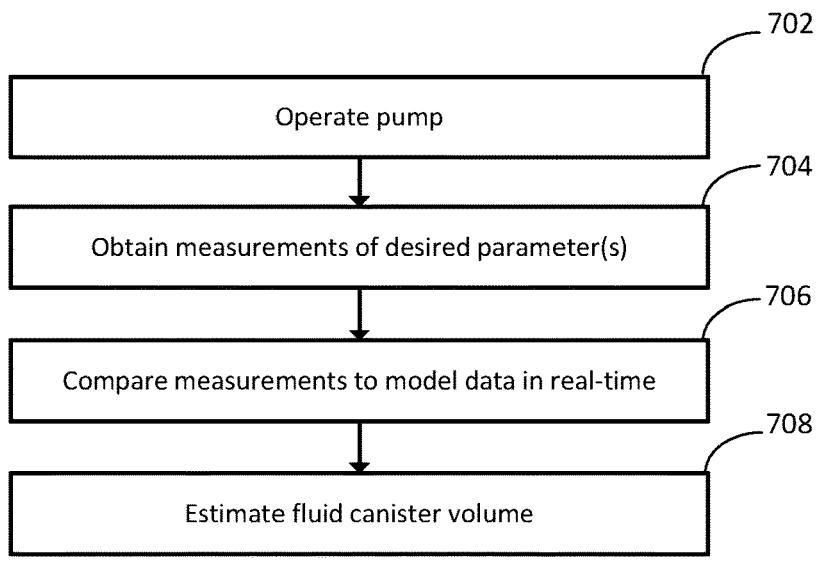
FIG. 7 is a flowchart of a method for estimating a fluid canister volume, according to an exemplary embodiment.

As an alternative to waiting until a predetermined parameter value has been attained during the drawdown of the negative pressure circuit (such as, e.g., described with reference to the method of FIG. 5) and/or as an alternative to waiting until a predetermined time interval has expired (such as, e.g. described with reference to the method of FIG. 6) to compare parameter measurement(s) obtained during draw down of the negative pressure circuit to previously obtained model data 148, as shown in FIG. 7, according to some methods, measured flow rate, pressure and/or pump ripple measurements may be compared in real-time to previously obtained model data 148. In such embodiments, a real-time comparison of the measured parameters to the model data may continue until sufficient data has been acquired to determine a statistically meaningful canister 106 volume estimate based on the identification of a model data decay curve that exhibits similar decay to that of the real-time parameter readings obtained at step 704. As will be understood, according to some such embodiments, any number of different types of statistical modeling and analysis may be used as real-time measurements are obtained at step 704 and compared against the model data at step 706 to address any noise in the acquired data and/or to address discrepancies or variations between the acquired parameter measurements and the model data 148.

Figure 8:
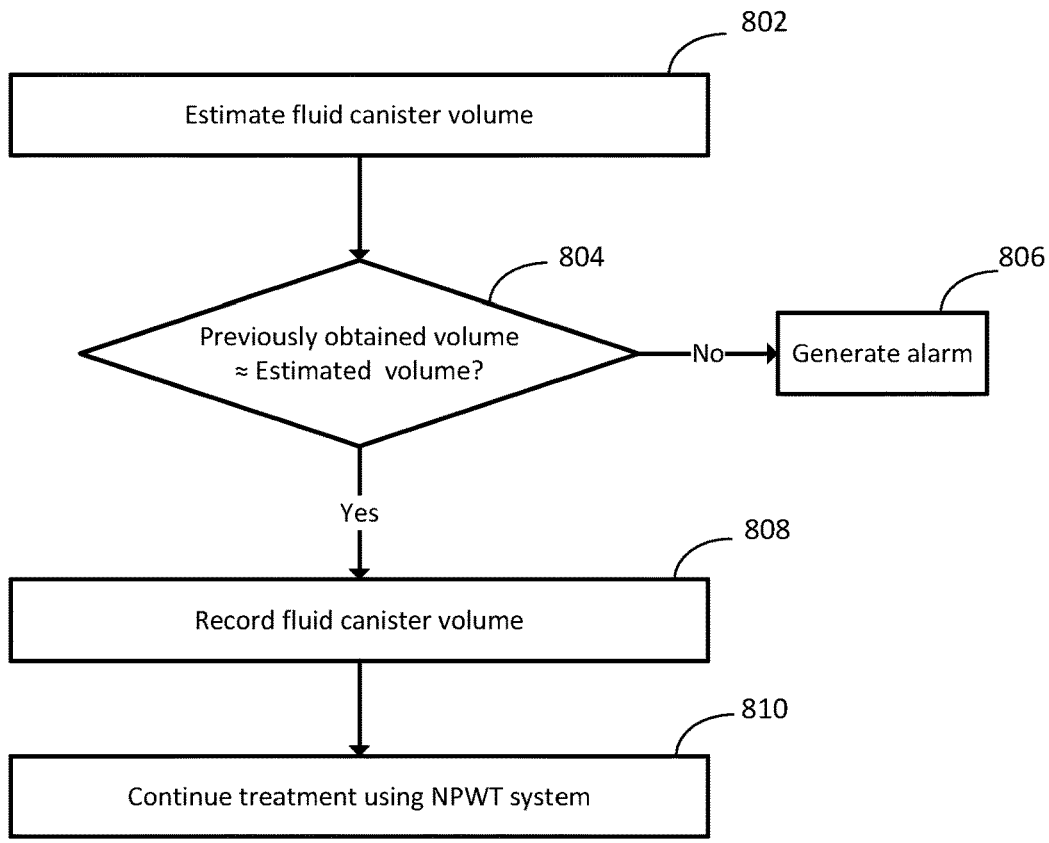
FIG. 8 is a flowchart of a method for verifying a volume of a fluid, according to an exemplary embodiment.

As noted above, according to various embodiments, the volume of the canister 106 attached to the therapy device 102 may have previously been obtained using any other number of markings provided on the canister 106 and/or other systems for measuring volume. In some such embodiments, it may be desirable to verify this previously obtained canister 106 volume using any of the methods described herein. For example, as shown in FIG. 8, in some such embodiments, after obtaining a canister 106 volume estimate at step 802 using any of the methods described herein, at step 804 the previously obtained volume measurement may be verified against the canister 106 volume estimated at step 802. At step 806, an alert may be generated in the event of a discrepancy between the canister 106 volume estimated at step 804 and the canister volume previously obtained using markings provided on the canister 106 and/or other systems for measuring volume. Otherwise, at step 808, the verified fluid canister 106 volume may optionally be recorded at step 808, and operation of the NPWT system 100 may continue at 810 as desired.

Figure 9:
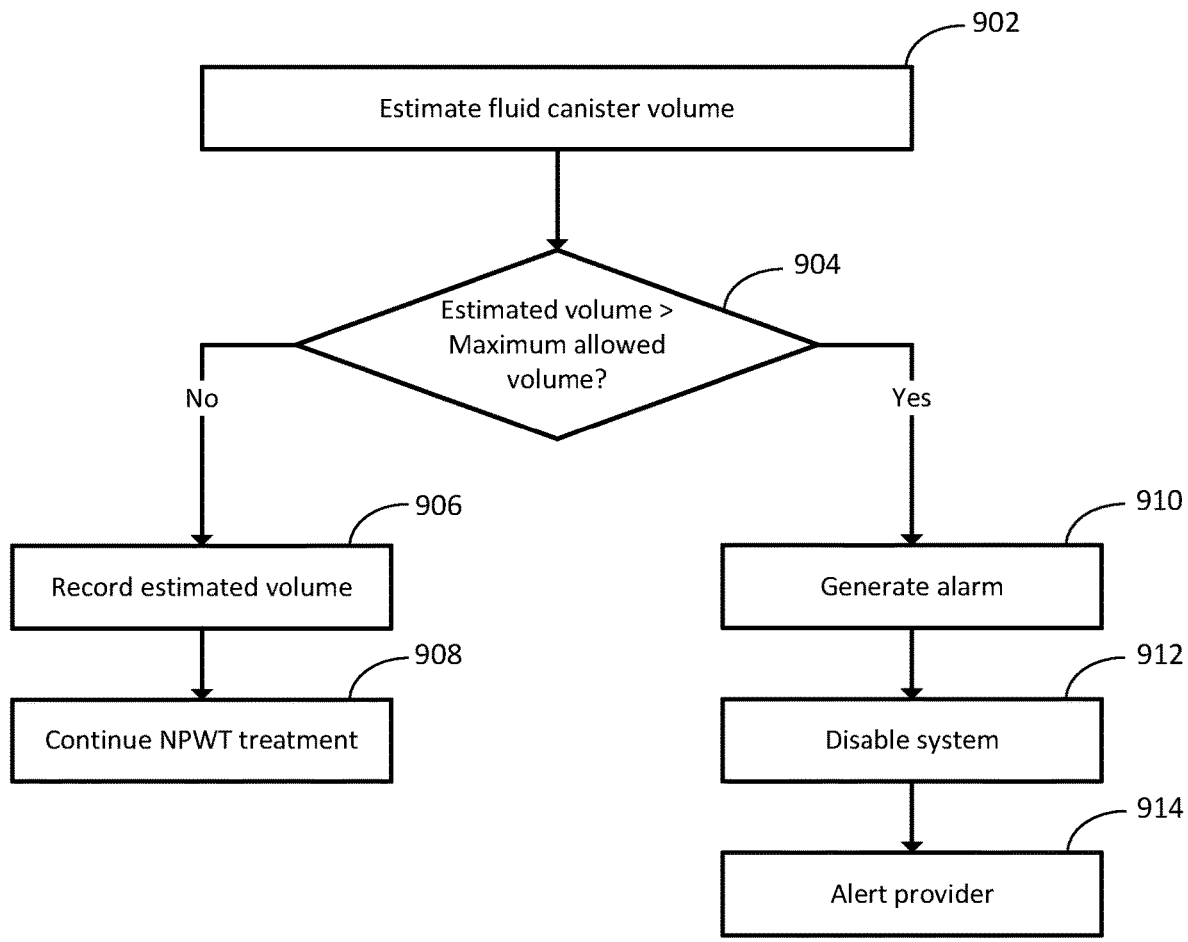
FIG. 9 is a flowchart of a method of operating a negative pressure wound therapy system, according to an exemplary embodiment.

As also discussed above, in certain situations (such as, e.g., during home-based use of the NPWT system 100), it may be advantageous to prevent use of the therapy device 102 with a fluid canister 106 having a volume that exceeds a predetermined threshold volume, such as, e.g. 500 mL. Accordingly, as illustrated by the method of FIG. 9, in some embodiments, after obtaining an estimate of the volume of a canister 106 at step 902 (using any of the methods described herein), at step 904 the estimated canister 106 volume may be compared against the predetermined maximum canister volume at step 904. Upon confirming that the canister 106 volume does not exceed the maximum allowed predetermined volume, at step 906 the estimated canister 106 volume may be recorded, and at step 908 operation of the NPWT system 100 may be continued as desired (such as, e.g., to provide NPWT to a patient in a home, or other medically unsupervised setting).

In the event that the volume of the canister 106 is determined to exceed the predetermined maximum volume at step 904, at step 910 an alert may be generated. The alert generated 910 at step may be communicated to one or both of the patient, a medical provider, and/or any other number of individuals that may be involved in the treatment provided by the NPWT system 100. In some embodiments, as an additional safety precaution, the NPWT system 100 may optionally be disabled (either permanently, for a predetermined time, or until re-enabled by an authorized user) to prevent the use of the NPWT system 100. In some such embodiments, at step 914 an alert indicating the disablement of the NPWT system 100 may optionally be provided to a medical provider and/or any number of other individuals that may be involved in the treatment provided by the NPWT system 100.

As will be understood, although the method of FIG. 9 has been described as being used to prevent the use of the NPWT system 100 with a canister 106 having an estimated volume that exceeds a predetermined maximum allowed volume, according to other embodiments, the method of FIG. 9 may be modified to instead be used to prevent the use of the NPWT system 100 in the event that the volume of the canister 106 is estimated to be less than a minimum, predetermined threshold volume.

In some situations, the volume of the canister 106 may be used solely for purposes of determining whether a canister 106 exceeds (or alternatively, is less than) an allowed (or required) threshold volume. Accordingly, as illustrated in FIG. 10, in some embodiments, a method of operating the NPWT system 100 may omit the step of estimating the volume of the canister 106, and instead may instead be configured to provide a binary assessment as to whether or not the volume of a canister 106 exceeds (or is less than) a threshold volume.

Figure 10:
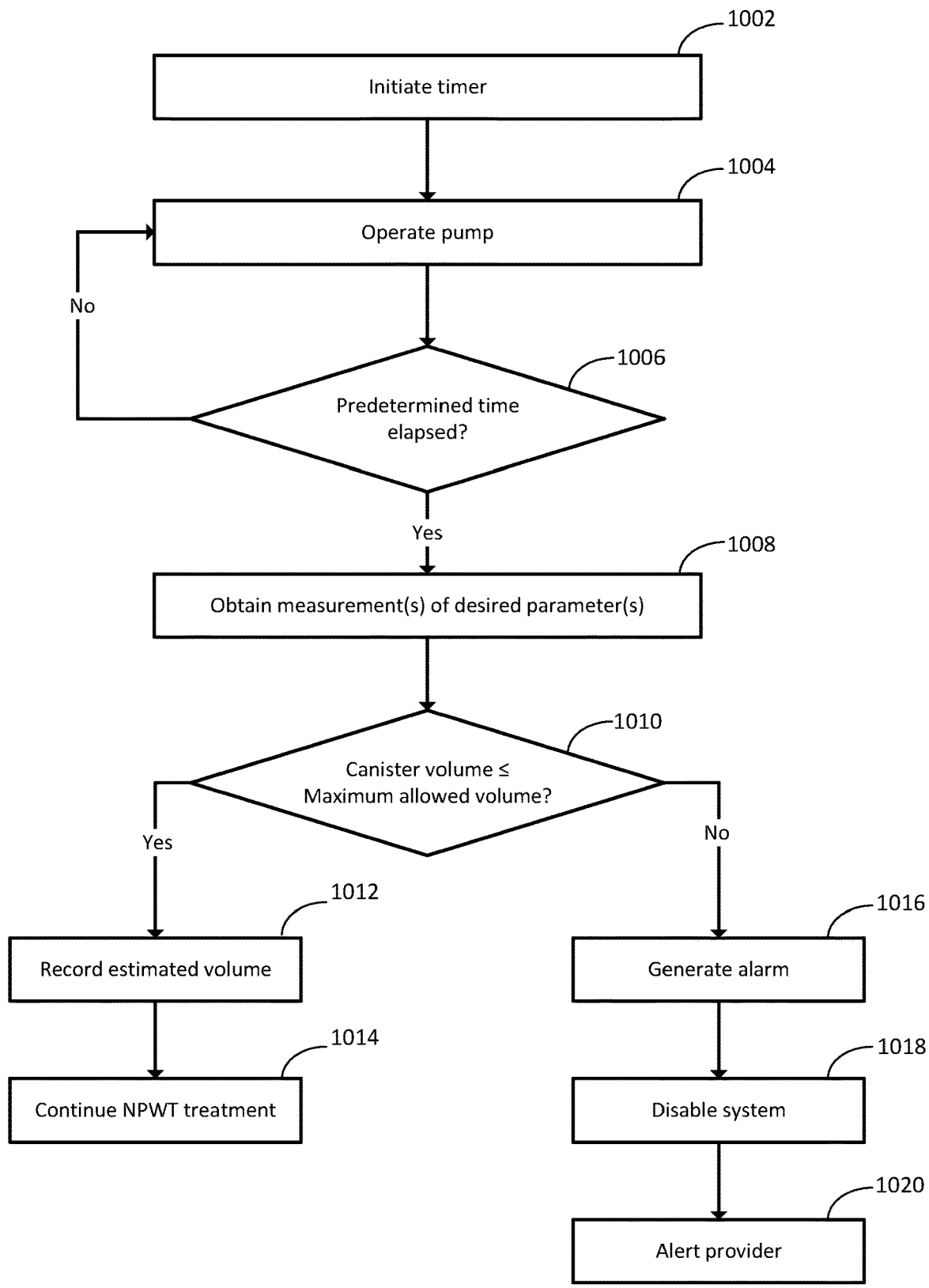
FIG. 10 is a flowchart of a method of operating a negative pressure wound therapy system, according to an exemplary embodiment.

As shown in FIG. 10, at step 1002 a timer may be set for a predetermined interval. Upon initiating the timer, operation of the pump 120 is initiated at step 1004. At step 1006, the pump 120 continues to operate until the expiration of the time interval set at step 1002, at which point, at step 1008, a measurement of at least one of the flow rate of air being evacuated from the negative pressure circuit, the pressure within the canister 106 and/or pump ripple is obtained.

At step 1010, the parameter measurement(s) obtained at step 1008 is compared against a threshold parameter value to provide a binary distinction as to whether the canister 106 volume exceeds a predetermined maximum volume. The predetermined parameter value against which the parameter measurement obtained at step 1008 is compared corresponds to the expected parameter value that would be measured during operation of the NPWT system 100 having a fluid canister defining the predetermined maximum volume at the same time following the initial operation of the NPWT system pump as the time interval at which the parameter measurement was obtained at step 1008. Depending on the parameter being compared, the determination of the measure parameter value being greater than or less than the threshold parameter value will be sufficient for the NPWT system 100 to determine whether to permit continued operation of the wound therapy system at step 1012 and 1014, or whether to generate an alarm at step 1016 and optionally disable the system at step 1018 and alert a provide or other individual at step 1020.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM. ROM, EPROM. EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A wound therapy system comprising:
a fluid canister;
a housing including a canister receiving attachment to which the canister is releasably secured;
a pump fluidly coupled to the canister and configured to draw a negative pressure within an interior of the canister; and
a controller configured to:
operate the pump to apply a vacuum to the interior of the canister;
obtain one or more measurements representative of a flow of air that is exhausted from the canister interior following the initiation of the operation of the pump; and
estimate the volume of the canister based on the obtained flow rate measurements;
wherein the controller comprises a memory storing model airflow curves representative of the flow of air that is exhausted from a canister interior during the operation of the wound therapy system with canisters defined by varying volumes.

2. The wound therapy system of claim 1, wherein the controller is configured to prevent operation of the wound therapy system in response to estimating that the volume of the fluid canister exceeds a predetermined volume corresponding to an upper limit of a quantity of fluid that may be safely evacuated from a patient.

3. The wound therapy system of claim 1, wherein the controller is configured to initiate a timer upon initiating operation of the pump.

4. The wound therapy system of 3, wherein the one or more measurements representative of the flow of air obtained by the controller comprise a flow rate measurement obtained at a predetermined time following the initiation of the operation of the timer.

5. The wound therapy system of claim 3, wherein the controller is configured to stop the timer and the operation of the pump in response to the controller obtaining a measurement that the flow of air is below a predetermined flow rate.

6. The wound therapy system of claim 4, wherein the controller is configured to estimate the volume of the canister by identifying a model airflow curve that is defined by a flow rate at the predetermined time that is substantially similar to the flow rate measurement obtained by the controller.

7. The wound therapy system of claim 5, wherein the controller is configured to estimate the volume of the canister by identifying a model airflow curve that is defined by a flow rate that is substantially the same as the predetermined flow rate at a time corresponding to the time interval defined between the initiation of the pump and the stopping of the pump.

8. The wound therapy system of claim 2, further comprising a flow restrictor positioned between a conduit second end and a canister inlet.

9. A method of estimating a volume of a canister attached to a negative pressure wound therapy device comprising:
attaching a first canister to a wound therapy device;

attaching a conduit between an inlet of the canister and a first wound dressing;

operating a pump of the therapy device to attain a desired predetermined negative pressure within a treatment space defined underneath the wound dressing;

obtaining one or more measurements of the airflow from an outlet of the canister following the initiation of the pump;

obtaining model airflow data curves representative of the change in the rate of airflow from a canister interior during the operation of a wound therapy system with canisters defined by varying volumes; and estimating a volume of the canister using the measured airflow and the obtained model airflow data curves.

10. The method of claim 9, further comprising generating an alert in response to determining that the estimated volume of the canister exceeds a predetermined volume corresponding to an upper limit of a quantity of fluid that may be safely evacuated from a patient.

11. The method of claim 9, wherein the volume of the canister is estimated by identifying a model airflow curve that is defined by a flow rate at the predetermined time that is substantially similar to the flow rate measurement obtained by the controller.

12. The method of claim 9, wherein the volume of the canister is estimated by identifying a model airflow curve that is defined by a flow rate that is substantially the same as the predetermined flow rate at a time corresponding to the time interval defined between the initiation of the pump and the stopping of the pump.

13. The method of claim 9, further comprising:
detecting a volume of the canister using one or more markers or indicators provided on the canister;
comparing the detected volume against the estimated volume; and
generating an alert if the detected volume and the estimated volume are not substantially the same.

14. A wound therapy system comprising:
a fluid canister;
a housing including a canister receiving attachment to which the canister is releasably secured;
a pump fluidly coupled to the canister and configured to draw a negative pressure within an interior of the canister; and
a controller configured to:
operate the pump to apply a vacuum to the interior of the canister;
obtain a measurements representative of at least one of a flow of air exhausted from the canister interior and a pressure within the canister interior following the initiation of the operation of the pump; and
estimate the volume of the canister based on the measurements;
wherein the controller comprises a memory storing at least one of model airflow curves representative of the flow of air that is exhausted from a canister interior, and model pressure curves representative of the change in pressure within a canister interior, during the operation of the wound therapy system with canisters defined by varying volumes.

15. The wound therapy system of claim 14, wherein the controller is configured to obtain measurements representative of both the flow of air exhausted from the canister interior and the pressure within the canister interior following the initiation of the operation of the pump.

16. The wound therapy system of claim 14, wherein the controller is configured to estimate the volume of the canister based on the measurements representative of both the flow of air exhausted from the canister interior and the pressure within the canister interior following the initiation of the operation of the pump.

17. The wound therapy system of claim 14, wherein the controller is configured to estimate the volume of the canister based on the measurements representative of only one of the flow of air exhausted from the canister interior and the pressure within the canister interior following the initiation of the operation of the pump.

18. The wound therapy system of claim 14, wherein the controller is configured to estimate the volume of the canister based on the measurements representative of the flow of air exhausted from the canister interior following the initiation of the operation of the pump.

19. The wound therapy system of claim 14, wherein the controller is configured to estimate the volume of the canister based on the measurements representative of the pressure within the canister interior following the initiation of the operation of the pump.

20. A method of estimating a volume of a canister attached to a negative pressure wound therapy device comprising:
attaching a first canister to a wound therapy device;
attaching a conduit between an inlet of the canister and a first wound dressing;
operating a pump of the therapy device to attain a desired predetermined negative pressure within a treatment space defined underneath the wound dressing;
obtaining measurements of at least one of the airflow from an outlet of the canister following the initiation of the pump and the pressure within an interior of the canister following the initiation of the pump;
obtaining model data curves representative of the change in at least one of the rate of airflow from a canister interior and the pressure within the canister interior during the operation of a wound therapy system with canisters defined by varying volumes; and
estimating a volume of the canister using the measurements and model data curves.

21. The method of claim 20, wherein the controller is configured to obtain measurements representative of both the airflow from the outlet of the canister and the pressure within the canister interior.

22. The method of claim 20, wherein the controller is configured to obtain model data curves representative of the changes in both the rate of airflow from the canister interior and the pressure within the canister interior during the operation of a wound therapy system with canisters defined by varying volumes.

23. The method of claim 20, wherein the controller is configured to estimate the volume of the canister based on the measurements and data curves representative of both the airflow from the outlet of the canister and the pressure within the canister interior.

24. The method of claim 20, wherein the controller is configured to estimate the volume of the canister based on the measurements and data curves representative of only one of the airflow from the outlet of the canister and the pressure within the canister.

* * * * *

UNITED STATES PATENT AND TRADEMARK OFFICE
CERTIFICATE OF CORRECTION

| | |
|---|---|
| PATENT NO. | : 11,266,770 B2 |
| APPLICATION NO. | : 16/365481 |
| DATED | : March 8, 2022 |
| INVENTOR(S) | : Christopher Brian Locke |

It is certified that error appears in the above-identified patent and that said Letters Patent is hereby corrected as shown below:

In the Claims

Column 18
Line 39, In Claim 4, delete "of 3" and insert -- of claim 3 --, therefor.

Signed and Sealed this
Ninth Day of April, 2024

*Katherine Kelly Vidal*

Katherine Kelly Vidal
*Director of the United States Patent and Trademark Office*